United States Patent [19]

Yang

[11] Patent Number: 5,445,941
[45] Date of Patent: Aug. 29, 1995

[54] METHOD FOR SCREENING ANTI-OSTEOPOROSIS AGENTS

[75] Inventor: Na N. Yang, Indianapolis, Ind.

[73] Assignee: Eli Lilly and Company, Indianapolis, Ind.

[21] Appl. No.: 81,610

[22] Filed: Jun. 21, 1993

[51] Int. Cl.$^6$ ............................................. C12Q 1/68
[52] U.S. Cl. ....................................... 435/6; 536/24.1
[58] Field of Search ................... 435/6, 7.2, 7.8, 172.3, 435/320.1; 536/24.1

[56] References Cited

U.S. PATENT DOCUMENTS

| | | | |
|---|---|---|---|
| 4,418,068 | 11/1983 | Jones | 514/337 |
| 5,183,736 | 2/1993 | Pfahl et al. | 435/6 |

FOREIGN PATENT DOCUMENTS

| | | | |
|---|---|---|---|
| 2210620 | 6/1988 | United Kingdom | C12N 15/00 |
| WO89/12101 | 6/1988 | WIPO | C12N 15/00 |
| WO91/01379 | 7/1990 | WIPO | . |
| WO92/00318 | 6/1991 | WIPO | C07K 3/20 |

(List continued on next page.)

OTHER PUBLICATIONS

Lewin (1990) "Genes IV". pp. 65–69. Oxford University Press New York, N.Y.

Berry et al (1990) EMBO J. 9(9), 2811–2818.

Turner et al. (1988) Endocrinol. 122(3), 1146–1150.

Reese and Katzenellenbogen, 1991, *Nucleic Acids Res.* 19(23): 6595–6602, "Differential DNA—binding abilities of estrogen receptor occupied with two classes of antiestrogens: studies using human estrogen receptor overexpressed in Mammaliam cells."

Colletta, et al., 1990, *Br. J. Cancer* 62: 405–409, "Anti-o-estrogens induce the secretion of active transforming growth factor beta from human fetal fibroblasts."

Gaub, et al., 1990, *Cell* 63: 1267–1276, "Activation of the Ovalbumin Gene by the Estrogen Receptor Involves the Fos-Jun Complex."

Love et al., 1992, *N. Eng. J. Med.* 326: 852–6, "Effects of Tamoxifen on Bone Mineral Density in Postmenopausal Women With Breast Cancer."

Love et al., 1991, *Annals of Int. Med.* 115: 860–864, "Effects of Tamoxifen on Cardiovascular Risk Factors in Postmenopausal Women."

ten Dike et al., 1990 *Molecular and Cell Biol.* 10(9): 4473–4479, "Recombinant Transforming Growth Factor Type $\beta 3$: Biological Activities and Receptor-Binding Properties in Isolated Bone Cells."

Pellerin et al., 1992, *Endocrinology* 181: 1094–1100, "Superinduction of c-Fos Gene Expression by Estrogen in Cultured Guinea-Pig Endometrial Cells Requires Priming by a Cycloheximide-Dependent Mechanism."

Klinge et al., 1992, *J. Steroid Biochem. Molec. Biol.* 43(4): 249–262, "Antiestrogen-Liganded Estrogen Receptor Interaction with Estrogen Responsive element DNA In Vitro."

Chambon, P., 1984, *Recent Prog. Horm. Res.* 40: 1–42, "Promoter Elements of Genes Coding for Proteins Modulation of Transcription by Estrogens and Progesterone."

Kumar et al., 1986, *EMBO J.* 5(9): 2231–6, "Localiza- (List continued on next page.)

*Primary Examiner*—Richard A. Schwartz
*Assistant Examiner*—Douglas Gurian-Sherman
*Attorney, Agent, or Firm*—James P. Leeds; Gerald V. Dahling; David E. Boone

[57] ABSTRACT

The present invention relates to methods for the identification of therapeutic agents for the treatment of osteoporosis and serum lipid lowering agents. The invention relates to isolating cloning, and using nucleic acids from the promoter regions of transforming growth factor $\beta$ genes comprising novel regulatory elements designated "raloxifene responsive elements". The invention also encompasses eukaryotic cells containing such raloxifene responsive elements operably linked to reporter genes such that the raloxifene responsive elements modulate the transcription of the reporter genes. The invention provides methods for identifying anti-osteoporosis agents that induce transcription of genes operably linked to such raloxifene responsive elements without inducing deleterious or undesirable side effects associated with current anti-osteoporosis therapy regimens.

5 Claims, 25 Drawing Sheets

U.S. PATENT DOCUMENTS

WO92/00330  6/1991  WIPO ............................ C07K 15/28
WO92/13063  1/1992  WIPO ............................ C12P 21/00
WO92/13091  1/1992  WIPO ............................ C12P 21/00

OTHER PUBLICATIONS tion of the oestradiol-binding and putative DNA-binding domains of the human estrogen receptor."

Krust et al., 1986, *EMBO J.* 5(5): 891-7, "The Chicken oestrogen receptor sequence: homology with v-erbA and the human oestrogen and glucocorticoid receptors."

Kumar, 1988, *Cell* 55(1); 145-56, "The Estrogen Receptor Binds Tightly to Its Responsive Element as a Ligand-Induced Homodimer."

Murdoch and Gorski, 1991, *Molecular and Cellular Endo.* 78(1991): C103-C108, "At the Cutting Edge: The role of ligand in estrogen receptor regulation of gene expression."

Ringold, 1985, *Ann. rev. Pharmacol. Toxicol.* 25: 529-66, "Steriod Hormone Regulation of Gene Expression."

Evans, 1988, *Science* 249: 889-895, "The Steroid and Thyroid Hormone Receptor Superfamily."

King, 1987, *J. Endocr.* 114: 341-349, "Structure and function of steroid receptors."

Fuller, 1991, *FASEB J.* 5: 3092-3099, "The steroid receptor superfamily: mechanisms of diversity."

Finkelman et al., 1992, *Proc. Natl. Acad Sci. USA* 89(24): 12190-3, "Ovarienctomy selectively reduces the concentration of transforming growth factor $\beta$ in rate bone": Implications for estrogen deficiency-associated bone loss.

Flaumenhalft et al., 1993, *J. Cell Biol.* 120(4): 995-1002, "Role of the Latent TGF-$\beta$ Binding Protein in the Activation of Latent TGF-$\beta$ by Co-Cultures of Endothelial and Smooth Muscle Cells."

Butta et al., 1992, *Cancer Res.* 52(15): 4261-4, "Induction of Transforming Growth Factor $\beta_1$ in Human Breast Cancer In Vivo following Tamoxifen Treatment."

Murphy et al., 1992, *J. Steriod Biochem. Mol Biol.* 41(3-8): 309-314, "Regulation of Transforming Growth Factor Gene Expression in Human Endometrial Adenocarcinoma Cells."

Gong et al., 1992, *Cancer Res.* 52(7): 1704-9, "Differential Effects of Estrogen and Aniestrogen on Transforming Growth Factor Gene Expression in Endometrial Adenocarcinoma Cells."

Saeki et al., 1991, *Mol. Endocrinol.* 5(12): 1955-63, "Regulation by Estrogen through the 5'-Flanking Region of the Transforming Growth Factor $\alpha$ Gene."

Knabbe et al., 1991, *Am. J. Clin. Oncol.* 14 Supp 2: 515-520, "Induction of Transforming Growth Factor $\beta$ by the Antiestrogens Droloxifene, Tamoxifen, and Toremifene in MCF-7 Cells."

Arrick et al., 1990, *Cancer Res.* 50(2): 299-303, "Differential Regulation of Expression of Three Transforming-Growth Factor $\beta$ Species in Human Breast Cancer Cell Lines by Estradiol."

Wakeling et al., 1989, *J. Mol. Endocrinol.* 2(3): 225-34, "Effects of antioestrogens on the proliferation of MCF-7 human breast cancer cells."

Noma Takafumi, 1991, *Growth Factors*, vol. 4, pp. 247-255, "Molecular Cloning and Structure of the Human Transforming Growth Factor-$\beta$ 2 Gene Promoter."

Mundy, Gregory R., *The Effects of TGF-$\beta$ on Bone* pp. 137-151.

Lafyratis, et al., *The Journal of Biological Chemistry*, vol. 265, No. 31, Issue of Nov. 5, pp. 19128-19136, "Structural and Functional Characterization of the Transforming Growth Factor $\beta$3 Promoter."

Kim, Seong-Jin, *The Jorunal of Biological Chemistry*, vol. 265, No. 31, Issue of Nov. 5, pp. 19128-19136, "Characterization of the Promoter Region of the Human Transforming Growth Factor-$\beta$ Gene."

Sporn, Michael B., *The Journal of Cell Biology, vol. 105, 1987, pp. 1039-1045*, "Some Recent Advances in the Chemistry and Biology of Transforming Growth Factor-Beta."

Massaque, Joan, *Cell*, vol. 49, pp. 437-438, May 22, 1987, "The TGF—$\beta$ Family of Growth and Differentation Factors."

Moses, Harold L., *Cell*, vol. 63, pp. 245-247, Oct. 19, 1990, "TGF—$\beta$ Stimulation and Inhibition of Cell Proliferation: New Mechanistic Insights."

FIG. 1A

```
-1362  GGATCCTTAGCAGGGAGTAACATGGATTTGGAAAGATCACTTTGGCTGCTGTGTGGGATAGATAAGACCGTGGGAGCCTAGAAAGGAGCTGGGTTGG
-1262  AAACTCTGGGACAGAAACCCAGAGAGGAAAAGACTGGGGCCTGGGGGTCTCCACTGAGTATCAGGGAGTGGGGAATCAGCAGGAGTCTGTCCCCACCCATC
-1162  CCTCCTTTCCCCTCTCTCTTCCTGCAGGCTGGCCCCGGCTCCATTTCCAGGTGTGGTCCCAGGACAGCTTTGGCCGCTGCCAGCTTGCAGGCTATG
-1062  GATTTTGCCATGTGCCCAGTAGCCCCGGCACCCACCAGCTGGCCTGCCCCCTGGGCAGTTGGCGAGAACAGTTGCACGGGCTTTCGT
 -962  GGGTGTGGGCCGCAGCTGCTGCATGGGACACCATCTACAGTGGGCCGACCGCTATCGCCTGCACACAGCTGCTGGTGCACCCGTGCACCTGAGATC
 -862  GGCCTGCTGCTCCGCAACTTCGACCGGTCTGAGGGACTCTGCCTCCAACGTCACCACCATCCACACCCCGACACCCAGTGATGGGG
 -762  GAGGATGCCACAGTGGTCAAGAGCACAGACTCTAGAGACTGTCAGAGCTGACCCCAGCTAAGGCATGCACCGCTTCTGTCCTTTCTAGGACCTCGGGT
 -662  CCCTCTGGGCCCAGTTTCCCTATCTGTAAATTGGGGACAGTAAATGTATGGGTCGCAGGGTGTTGAGTGACAGGAGCTGCTTAGCCACATGGGAGGTG
 -562  CTCAGTAAAGGAGAGCAATTCTTACAGGTGTCTGCCTCCTCCCCACCCTCCAGTGTCCTCCTGACCCTTCCATCCCTCAGTGTCCTCCCCACTGACACCCTCCGGAGGC
```

FIG. IB

```
-462  CCCCATGTTGACAGACCCTCCTTCTCCAGCCTGACTCCTTCCGTTCTGGTGTCGACTCCTCTGGTCCCCTGTCTCATC
-362  CCCCGGATTAAGCCTTCTCCGCTGGTCCTCTTTCTCGGTGACCACAGCCCGCCAAAGCCACAGCGCATCTGATCACCCGCTTGTGGCGCTTGG
-262  CCGCCAGGAGGCAGCACCCTGTTTGCGGGGCGGAGCCTTTCCCCAGGCTGAAGGACCCCCCCGGCCGGGAGCCCGAGCGCCACGCGAGA
-162  TGAGGACGGTGGCCAGCCCCCCATGCCCGCGCCCCCCTGGGCGCCCCTGGGTGGGGCTTCAAAACC
-62   CCCTGCCGACCCAGCCGGTCCCCGCCGCCCCGGCCCATCTCCCTCCCCAGCAGCCAGACAGCGCCGAGGCCCCG
39    GCCGGGGGCAGGGGACGCCCCGTCTGAGCGCTCGGCTCCGGAGCCCGAGCGGGGAGGAAGGAGTCGCCGAGGA
139   GCAGCCTGAGGCCCCAGAGTCTGAGACGAGCCCGCCGCCGCCGCACTGCGGGAGGCCGGGGACCTCTTGGCCGCTGCCGGAGCCGAGACTGGGAG
239   AAGAGGAAAAAAACTTTGAGACTTTCCGTTGCCGCTGGGACGCTGCCCCGGGACCCCGAGGAGGCAGGACTTGGG
339   GACCCCAGACCGCTCCCTTTGCCGCGGGACGCTTGCTCCCCTGCCGGTCCTCCCCTACACGGCGTCCCCAGGCGCCCCAGCCCTCGGGA
439   GTCGCCGACCCGGCTCCCGGCCTCCCCGCCAAAGACTTTTCCCCAGACCTCGGGCGCACCCCGCCCTTCATCCCCGCGCCTTGCTGTCTCCTGAGCCCCGGCAT
539   CCTAGACCCCTTTCTCCTCCAGGAGACGGATCTCTCTCCGACCTGCCACAGATCCCCTATTCAAGACCACCCACCTTCTGTGTACCAGATCGCCGCCATCTA
```

FIG. IC

```
639 GGTTATTTCCGTGGGATACTGAGACACCCCCGGTCCAAGCCTCCCCTCCACCACTGCGCCCTTCTCCCTGAGGAGCCTCAGCTTTCCCTCGAGGCCCTCC

739 TACCTTTTGCCGGGGAGACCCCCCAGCCCCTGCAGGGGCGGGGCCTCCCCACCACCAGCCCCTGTTCGCGCTCTCGGCAGTGCCGGGGGGCCGCCTCCC

Met
839 CCATG
```

FIG. 2A

```
-2277 AAGCTTTTACCAATACCTCCCGTCTTACCCCTCCTGGGCTTTGGGAAATTAAAGTAGCCTCTTATGAGTAAGTCAG
-2200 GGGTCTCAGGTCTAAGGAGTTGTTAAGTGAGCAATAGTAGCTACTCAGTAAACTAAGTATTATGAACAAAAGTGTGTATGTCTATGTCAGGAAGAGGGGTGGC
-2100 CATCAGAATTTATGGCTTGCGCTGTTTCCTAGAAGTGATGTAATGAACTTTTGCTACTCTATCCACACTCTAATCTGAATCTACTTAAGGTGCATCAGTG
-2000 TCTGTACCAAGAAGGTTGTCTATAAACATGAAAGATGCTCACTGGCTTGTGGAAGCTGAACCTGTATCCTCAGAAAATACAGTGATAGCTAATTCA
-1900 GGTAACCAGCCATATTCCACAGCAGCATCTTCTCTCAGTAGCTCTGGTTTGGAGCTCCTGTGTCTATAATGCCACAGGTGTAAGATATTCACT
-1800 TTTTGTCCAATCTGTAGAGCTAGCCTACTGCAGTTCTCAAACTGAACTCAGAGGGGAGGACCTAACTGGATGAAACTACTAGTCTGACAGTAGCCGCCTCTT
-1700 GATTATCTTTTCTGGGCTACTGGGATGGTAGCTTTGCTTCAACTCAAAACTGGTATCAAGGAAAGGAACCTGCTGGTGCTGATTTATACATAATTTTT
-1600 AGAATTATTCAGAAGTGGGTTGGAACAATTATTTTATTCCAGAGTTTTTCAATGTGTGATAATGGAAAAAATTCTGTATTCAAGGGAGTTTGGAAAATGC
-1500 TGGGTTAAAAGAGTGAAAGGTTTTCTCTTCTACAGGAGTTTCAGAGCCTTTAACATGATAATGTTCCAGAATGAGGAATCTAAGAGGACAGGAGAGTAC
-1400 CCAGTATCTCCCAAACTGTTTGACTCCAGAATTCCTGTTGTCAGAACATATTCTGGGACCATTGTTTCTCAGAAGTACATAGTAGTAAGAACATAGT
```

FIG. 2C

```
-300  GGGAGGCTGTGACTGAGCTACACTAAGTAAAAACGGGAGACTTGATTGTCCTTCAACAGACCTGTCCAAATGACTGAAGTAAATACCGTAAATCACT
-200  GTTGTCAGGGCGCACATTCCACCTCCTTCCTCCCTTACCCACAGGGTCCACATTTCCACACTCCCTACACGGTTCGGGGAGAGCTCGTGGTCTAAGTAA
-100  CGAGAGGAGACTTCTGACTGTAATCCTAGCACGTCACTTTGTTGAAGGCAGACACGTGGTTCAGAGAGAACT TATAAA TCTCCCCCTCCCCGAAGATCGTG
  -1  ATGTTATTCGCTGGCAGCAGAAGGTCTTGCCCAGCGAGCTCCAGAAGCGTCCTGACAAGAGAAAGACAGATTGAGATAGAAGAGAAAGAGAGAA
 101  AGAGACAGCAGAGCGCAAGTGAAGAGGCAGGGGATGGAGCATATTACGTGACCGGCCTAGGGAGTCATCCAGGAACAAACTGAG
 201  GGGCTGCCCGGCTGCAGAGAGGAGACAGAGGATCTATTTTAGGGTGGCAAGTGCCTCCTAAGCCTACCCTAAGCGAGCAATTCCACGTTGGGAGAAGCCA
 301  GCAGAGGTTGGGAAAGGGTGGAGTCCAAGGACGCCCCTGCCAACTCCCTCAGAATAAAACTCCCCAGCCAGGGTGTCGCAAGGCTGCCGTTGTGA
 401  TCCGCAGGGGTGAACGCGCAACCCGCTGATCGTATGTGGCTGGCTCGGGTTGCCGTTGGCAGCAAGAGAGGAGCAGGAAGGAGGGAGCTGGAGGC
```

FIG. 2D

```
 501 TGGAAGCCGTTTGCAAGCGGGCCAGCAACGTGGAGTAACCAAGCGGGCGCCGCCAGGTGTAGGCCACGGGCCAGCTCCCAGAGCA
 601 GGATCCGCCCGCCCCTCCGCAGCCTCTGCGGGCTGCCCTGCCGGCACCCGAGTACCGAGCGCCTCCTCCCCGGTGGCTGGGCTC
 701 GCCCCAGCGGCGCCACACGCCACACACACACACACACACGCGTCGTTCCTGCTCCGGAGCTGCTCCTGCTCTCAGCGC
 801 CGCAGTGGAAGGCAGGACCCGAACCGCTCCAGGTCAGCCCCAGGTCAGATCCCGCCACTCCGCACCCGAGACTGACACAC
 901 TCAGTTCGCCCAGCTGCCCCGGGACCTTTCATCTCTTCCCTTTTGCCGGAGAGCCGAGTTCAGATCCCGCCACTCCGCACCCGAGACTGACACAC
1001 TGAACTCCACTTCCTCCTCTTAAATTTATTTCTACTTAATAGCCACTCGTCTCTTTTTCCCCATCTCATTGCTCCAAGAATTTTTTCTCTTACTCG
1101 CCAAAGTCAGGGTTCCCTCTGCCCGTCCCCTATTAATATTTCCACTTTTGGAACTACTGGCCTTTTCTCTTTTAAAGGAATTCAAGCAGGATACGTTTTTC
1201 TGTTGGGCATTGACTAGATTGTTTGCAAAAGTTTCGCATCAAAAACAACAACAACAACTCTCCTTGATCTATACTTTGAGAATTGTTG
                                                                         Met His Tyr Cys Val Leu Ser Ala Phe Leu Ile
1301 ATTTCTTTTTTTATTCTGACTTTTAAAAACAACTTTTTTTCCACTTTTTTTAAAAAATG CAC TAC TGT GTG CTG AGC GCT TTT CTG ATC
```

FIG. 3A

```
  1 CAGTAGTAGC TTCCAGAACT TGCTTAGCAC CTGAATCACG TGTGAGGTTT

51 GTAAAGAAAC AGAGATGCCA GGGCCTCAGC TCTGGAGACT GATTGGTAGA

101 GGTGGAGTCC AAAAAGTAT AACTTTAATA ATTTTCCTTC CTATCTTCAA

151 CTGTCTGCTC AAAGGCCTTC CCTTATCACC CTATTTGAAA CTGCAACATC

201 CCCCAACCTA GGCACACCCC ATCCTCCTTC CCTGCTTGAT TTTCTGCCAC

251 ACCACATTTG TTTGTTTGCT TGTCTGTTTG AGACACGGTC TTGCTCTGTC

301 GTCCAGGCTG GAGTGCAGTG GTGCAATCTT GGCCCCTGT AAACTCGCCT

351 CCCTGGCTCA AGTGATTATC CTGCTCAGCC TCCCAAGTAG ATGCGTGCGC

401 CAACATGCCG GGCTAATTTT TCCATTTTTT TGTAGAGACT GGGTTTCGCC

451 GTGTTGCTGG GGCTGGTCTC GAATTCCTGA GCTCAAGTAA TCCTCCTGCA

501 TGGGCCTCCC CAAATGCTGG GATTACAGGC GTGAGCCACT GCACCTGGCT

551 CAGCACTTTT TACCGTACTA CATCATTTAC ATATTTATTT AGTTTATCGC

601 CTCCTCCACT GCCCCACCCC TGCCTCTAAA TAAAATTTCC CTGAGGGCAG

651 GAGTTTTGTT TCGTTCACTG ATATTCTTCA CAGAGCCTAG AATAGTGCCT

701 GGTATATAGA AACATTAAAC TTTTTCTGAA ATTTCAGAGG CAGTATAGCA

751 TAGTAATTAA GTCCAGAATC TGGCAACGTC CTGGGTGCAA ATCCAACAG

801 CTGACACCTA ATAACTATGT GACCTTGGGC AAGTTACTTT TAAAGTTTCT
```

FIG. 3B

```
 851 ACCCCTAGGT TTCCCATTGG TTTTGCAAAT GAAAGTAATG CCTACCCAAG

901 CTAGATAGCC TGTGTAAATA TCGCCTCCAT CACTCACAAG CAGTGTGGTC

951 TGTAAAAAAA AAAACAAAAA ACTCTATGCC TCAGTTTCCT CATCCGTAAA

1001 AGTGACCCAC CGCTGTGCTG GGATACAGAG AACAGCCCCT TCAGTTAGTG

1051 GCCTGGAAGC CAGCCTCTCA GAAAGGGTCC AGGAAGGCTG GAGTGAGATG

1101 GGGTGGAGCG GCACTCACTC TCAGGAAAGT TCAGTTCAGA GGCAAGCCCT

1151 GTGTTGCGGG GTGCGGGGAG CCACGTGCCC TACCCTCCCT TGGCTGCTCG

1201 TGGGAAAAGG CCTAGAGGTT CGGGCCGAGA AGAGGAGCGA AAGCACAGAG

1251 CCGACTTCCC CTCACCCATC TGGGAAATGG CTCGGGCCAA CTGCTGACTT

1301 CGCGCTCGCT GGCCGACGTC CTGCGGAGAC CTCGGCGGGG AGGGAGGCTG

1351 AACATCTGGA TGACATTTCT GCGAGAGAGC GGCTCCGGAG CGGCGGTCGG

1401 GGAGGGAGAG CTGCTCGTGC GCACGTCGGG CCGGGAGGGA GGCGATTCCT

1451 CGGGGCCTGG GTCTTGTTTT TCTCGCTCTC TACCGCAGCC CCTTCTCCCG

1501 CCCCTCAGCC CCCACCCCGC AGCCCCCAGC CCCCGAGCCT CCCCGGCTCC

1551 CGACCAGCCG AGCTCCTTCA CTGGCGGCCT CCGCTCGCCA GAGGGCACCC

1601 TCGATCTTCC GGAAAACGCC ACCATTTTTC ACTGCCCCTG GAGCGTCTCC

1651 AGGCTTCTGC CCGCCTCCCG ACTCCGATCT TGTCAATGAA GAATCGGGCC
```

FIG. 3C

```
1701 AGGATCGCCG CGGAGCGGAC GCCGACCCTC CGACCCGGCT CGCAGGCTGG

1751 GAGTCCCCTC TGCGAGGCTG GCATGGCCGC CCCTACCGGG TCCCGCGCCC

1801 TCTGCGGACC CTCCCCGGGT TGGGCCTGGC CGCGGGCGGC CCCGGGACCG
                                                   -301
                                                    ↓
1851 GGGGACCAGG AGGGAGAGTA GACCGGGCCG GACGGCGCGG ACTGACAGCT

1901 GGCGAGAGGG CGCCGGGGCT GGGGGAAAGG GAGGGAGGGG GCTCATCGGA
                              -221
                               ↓
1951 GTAACTTTCC AGAAAAACAC CAACGTGTGG CAGGAGTGAT TCCAAGAGGG

2001 GAAAAAAAGT TCAGCTACCA CGTCGAACGA GAGGACTCGC AAAGTATTTT

2051 TCAAAAGGGC TCGGCTTTTC CTGTGCCTGT TTAAAACATT AACATCGTGC
       -91                                  -60         -47
        ↓                                    ↓           ↓
2101 AGCAAAAGAG GCTGCGTGCG CTGGTCCCTC CCTCCCCAC CCCAGGCCAG
       -38                                              +1
        ↓                                                ↓
2151 AGACGTCATG GGAGGGAGGT ATAAATTTC AGCAGAGAGA AATAGAGAAA
                                    +35
                                     ↓
2201 GCAGTGTGTG TGCATGTGTG TGTGTGTGAG AGAGAGAGGG AGAGGAGCGA
                            +75
                             ↓
2251 GAGGGAGAGG GAGAGGGAGA GAGAGAAAGG GAGGGAAGCA GAGAGTCAAG
       +110
        ↓
2301 TCCAAGGGAA TGACCGAGAG AGGCAGAGAC AGGGGAAGAG GCGTGCGAGA

2351 GAAGGAATAA CAGCAGCTTT CCGGAGCAGG CGTGCCGTGA ACTGGCTTCT

2401 ATTTTATTTT ATTTTTTTCT CCTTTTTATT TTTAAAGAG AAGCAGGGGA

2451 CAGAAGCAAT GGCCGAGGCA GAAGACAAGC CGAGGTGCTG GTGACCCTGG

2501 GCGTCTGAGT GGATGATTGG GGCTGCTGCG CTCAGAGGCC TGCCTCCCTG
```

FIG. 3D

```
2551 CCTTCCAATG CATATAACCC CACACCCCAG CCAATGAAGA CGAGAGGCAG

2601 CTGAAAAAGT CATTTAGAAA GCCCCCGAGG AAGTGTAAAC AAAAGAGAAA

2651 GCATGAATGG AGTGCCTGAG AGACAAGTGT GTCCTGTACT GCCCCACCTT

2701 TAGCTGGGCC AGCAACTGCC CGGCCCGCTT CTCCCCACCT ACTCACTGGT

2771 GATCTTTTTT TTTTTACTTT TTTTTCCCTT TTCTTTTCCA TTCTCTTTTC

2801 TTATTTTCTT TCAAGGCAAG GCAAGGATTT TGATTTTGGG ACCCAGCCAT

2851 GGTCCTTCTG CTTCTTCTTT AAAATACCCA CTTTCTCCCC ATCGCCAAGC

2901 GGCGTTTGGC AATATCAGAT ATCCACTCTA TTTATTTTTA CCTAAGGAAA

2951 AACTCCAGCT CCCTTCCCAC TCCCAGCTGC CTTGCCACCC CTCCCAGCCC

3001 TCTGCTTGCC CTCCACCTGG CCTGCTGGGA GTCAGAGCCC AGCAAAACCT

3051 GTTTAGACAC ATGGACAAGA ATCCCAGCGC TACAAGGCAC ACAGTCCGCT

3101 TCTTCGTCCT CAGGGTTGCC AGCGCTTCCT GGAAGTCCTG AAGCTCTCGC

3151 AGTGCAGTGA GTTCATGCAC CTTCTTGCCA AGCCTCAGTC TTTGGGATCT

3201 GGGGAGGCCG CCTGGTTTTC CTCCCTCCTT CTGCACGTCT GCTGGGGTCT

3251 CTTCCTCTCC AGGCCTTGCC GTCCCCTGG CCTCTCTTCC CAGCTCACAC

3301 ATG
```

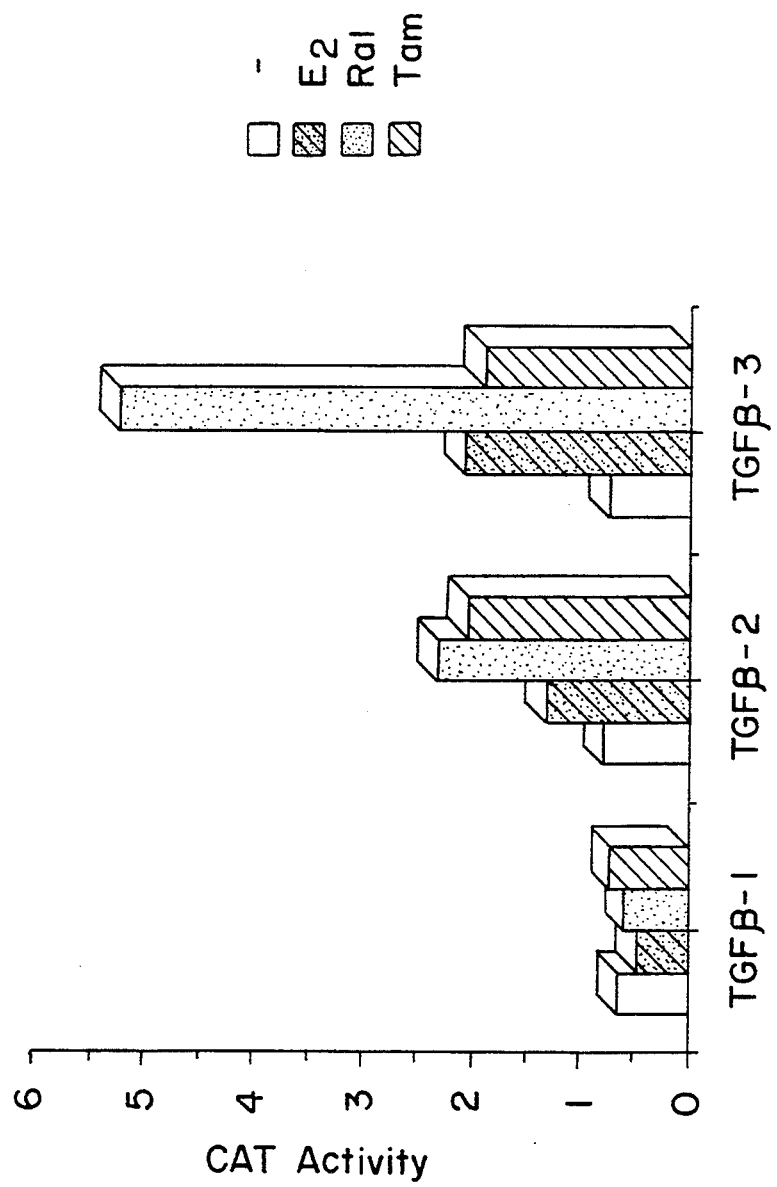

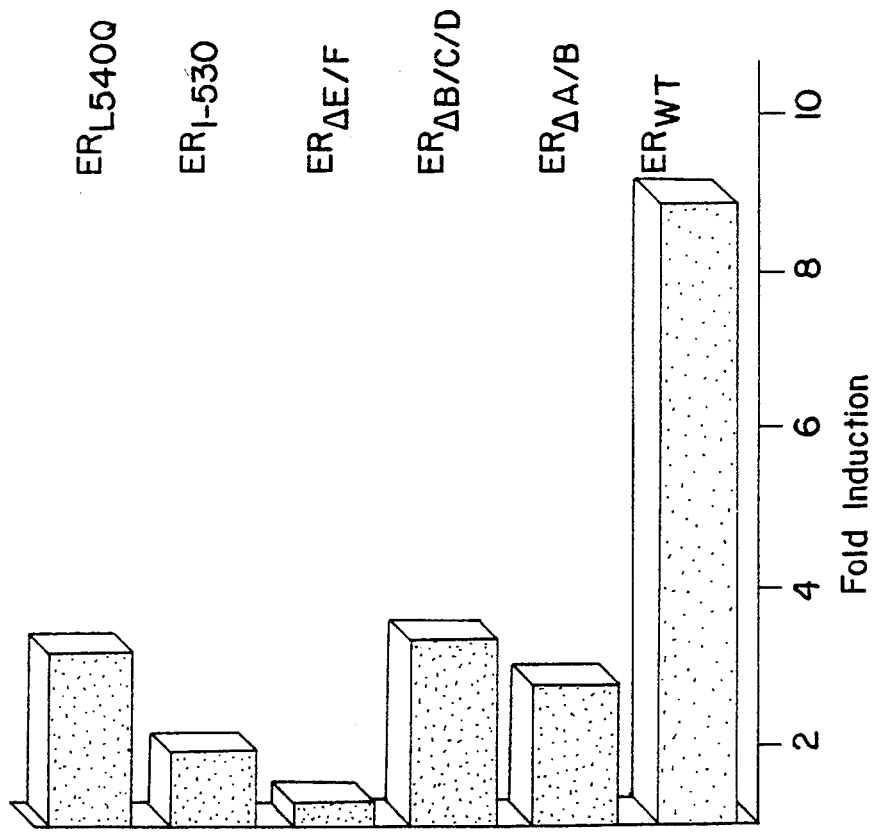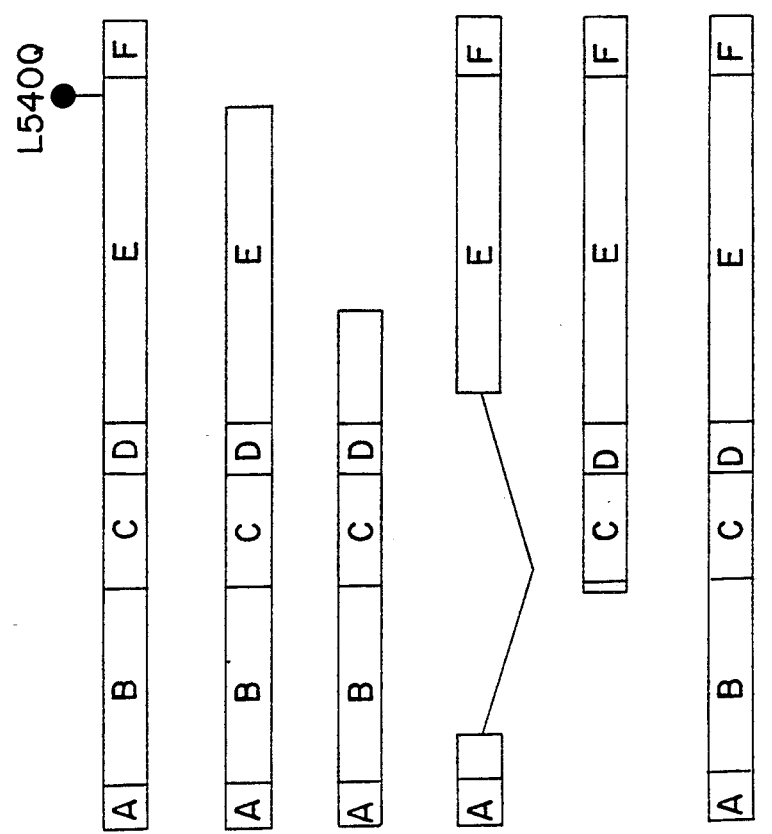
FIG. 7

METHOD FOR SCREENING ANTI-OSTEOPOROSIS AGENTS

BACKGROUND OF THE INVENTION

1. Field of the Invention

The invention relates to methods for identifying therapeutic agents for the treatment of osteoporosis and as serum lipid lowering agents. The invention relates to isolating, cloning and using nucleic acids comprising the promoter regions of mammalian transforming growth factor B genes that are novel regulatory elements designated "raloxifene responsive elements". The invention also encompasses genetically engineered eukaryotic cells containing the recombinant expression constructs wherein the raloxifene responsive elements are operably linked to reporter genes. In such cells the raloxifene responsive elements are capable of modulating transcription of the reporter genes and response to treatment with certain compounds. The invention also relates to methods for identifying anti-osteoporosis agents that induce transcription of certain genes via raloxifene responsive elements and that specifically do not induce deleterious or undesirable side effects that have been associated with estrogen replacement therapy, such as increased risk with uterine and breast cancer. The nucleic acids, cells and methods of the invention provide effective methods for screening putative sources of anti-osteoporosis agents or serum lipid lowering agents and identifying those that advantageously lack the undesirable side effects associated with current anti-osteoporosis agents.

2. Background of the Related Art

In 1991, U.S. pharmaceutical companies spent an estimated $7.9 billion on research and development devoted to identifying new therapeutic agents (Pharmaceutical Manufacturer's Association). The magnitude of this amount is due, in part, to the fact that the hundreds, if not thousands, of chemical compounds must be tested in order to identify a single effective therapeutic agent that does not engender unacceptable levels of undesirable or deleterious side effects. There is an increasing for economical methods of testing large numbers of testing large number of chemical compounds to quickly identify those compounds that are likely to be effective in treating disease. At present, few such economical systems exist.

A. Bone Loss

One disease that conspicuously lacks a rapid method of potential therapeutic agents is bone loss. Bone loss occurs in a wide variety of patients, including those who have undergone hysterectomy, who are undergoing or have undergone long-term administration of corticosteroids, who suffer from Cushing's syndrome or have gonadal dysgenesis, as well as post-menopausal women.

The mechanism of bone loss is not well understood, but in practical effect, the disorder arises from an imbalance in the formation of new healthy bone and the resorption of old bone, skewed toward a net loss of bone tissue. This bone loss includes a decrease in both mineral content and protein matrix components of the bone, and leads to an increased fracture rate of the femoral bones and bones in the forearm and vertebrae predominantly. These fractures, in turn, lead to an increase to general morbidity, a marked loss of stature and mobility, and in many cases, an increase in mortality resulting from complications.

Unchecked, bone loss can lead to osteoporosis, a major debilitating disease who predominant feature is the loss of bone mass without a reduction in bone volume (by decreased density and enlargement of bone spaces), producing porosity and fragility. Osteoporosis among post-menopausal women is one of the most common types of bone, affecting an estimated 20 to 25 million women in the United States alone.

A significant feature of post-menopausal osteoporosis is the large and rapid loss of bone mass due to the cessation of estrogen production by the ovaries. Indeed, data clearly support the ability of estrogens to limit the progression of osteoporotic bone loss, and estrogen replacement is a recognized treatment for post-menopausal osteoporosis in the United States and many other countries.

Although estrogens have been beneficial effects on bone, given even at very low levels, long-term estrogen replacement therapy has been implicated in a variety of disorders, including an increased risk of uterine and breast cancer. These serious side effects cause many women to refuse this treatment. Recently - suggested alternative, therapeutic regimens, designed to lessen the cancer risk, such as administering combinations of progestogen and estrogen, cause some patients to experience regular withdrawal bleeding, which is unacceptable to most older women. Concerns over these significant undesirable side effects associated with estrogen replacement therapy, and the limited ability of estrogens to reverse existing bone loss, provide a strong impetus to the development of effective alternative therapies for bone loss that do not cause undesirable side effects.

B. Antiestrogens

Another approach in osteoporotic therapy is the use of antiestrogens. In general, antiestrogens inhibit (antagonize) the activity of estrogen in the body. Antiestrogens bind to the estrogen receptor, although it is believed that the interaction between antiestrogens and the estrogen receptor involves a different domain of the receptor than that to which estrogen binds. Some antiestrogens, on the other hand, display pharmacological properties that are a mixture of agonist and antagonist properties. In other words, these compounds cause certain effects that mimic estrogen, while antagonizing other effects that are commonly associated with estrogen administration in cells that express the receptor. Because of this mixed effect of some antiestrogens, they are subject to the same adverse effects associated with estrogen replacement therapy.

One antiestrogen known to display such a mixed agonist/antagonist effect is tamoxifen, a drug used for the treatment of breast cancer. Tamoxifen acts as an estrogen antagonist in its ability to reduce the growth of breast tumors, but it also acts as an agonist in its ability to reduce the growth the serum cholesterol in both healthy women and women with breast cancer. (Love et al., 1991, Annals Int. Med. 115: 860–864) and to increase bone density in breast cancer patients (Love et al., 1991, N. Eng. J. Med. 326: 852–856. At least one study has suggested that the increases in bone density possible with tamoxifen appear to be restricted to the lumbar spine, with bone loss being reported in the radius in some breast cancer patients treated with tamoxifen. Furthermore, tamoxifen treatment has also been suggested to contribute to weight gain among postmenopausal women. Love et al., 1991, Ann. Int. Med. ibid.

Improved anti-osteoporotics that achieve increases in bone density without causing negative side effects are clearly needed. Unfortunately, no method currently exists for rapidly and efficiently screening large number of compounds to identify those that display the desired anti-osteoporotic effects. Because this screening process comprise the most time-consuming and expensive step and identifying improved anti-osteoporotic compounds, development of a rapid method for testing a large numbers of compounds to identify those that are likely to possess anti-osteoporotic effect is highly desirable.

C. Interaction with Estrogen Receptor

It is well established that estrogens exert their effects by first binding to an estrogen receptor, and then the estrogen/estrogen receptor complex binding to DNA. The hormone/receptor complex modulates gene expression via this DNA binding. Kumar, 1988, Cell 55: 145–156. Antiestrogens also bind to estrogen receptor. Although these antiestrogen/receptor complexes bind to DNA they generally fail to modulate gene expression. Both estradiol/estrogen receptor complexes and hydroxytamixofen/estrogen receptor complexes bind in vitro to DNA binding domains called estrogen responsive elements. Kumar, 1988, ibid.

The conformation of the ligand/receptor complex is a matter of some debate. However, recent studies have suggested a conformational difference between estrogen receptor bound to estradiol and the same estrogen receptor bound to 4-hydroxytamoxifen or ICI 164,384. Klinge et al., 1992, J. Ster. Biochem. Mol. Biol. 43: 249–262.

D. Transforming Growth Factor $\beta$

In an effort to rationally address the problem of developing improved anti-osteoporotic agents, researchers have investigated proteins known to play a role in bone maintenance. One protein known to influence bone remodelling and bone turnover is transforming growth factor $\beta$. Although commonly referred to as a single compound, "TGF$\beta$" is actually a family of molecules that now is known to include at least three isoforms: TGF$\beta$-1, TGF$\beta$-2 and TGF$\beta$-3. See, Arrick et al., 1990, Canc. Res. 50: 299–303.

The present inventor has noted that ovariectomy induces a significant decrease in TGF$\beta$-3 in rat bone (data collected by present inventor is unpublished); others have noted the same type of correlation with respect to levels of TGF$\beta$ (isoform not specified), Finkelman et al., 1992, Proc. Natl. Acad. Sci. USA 89: 12190–12193. Further, the present inventor has noted that administration of raloxifene, an antiestrogen, to such rats restores TGF$\beta$-3 concentrations to levels equal to or higher than that found in control animals. The direct correlation between TGF$\beta$-3 levels and circulating levels of estrogen or antiestrogen, and the finding that TGF$\beta$ (isoform not specified) plays a significant role in bone remodelling and turnover, Noda et al., 1989, Endocrin. 12: 2991–2994, suggest that osteoporosis may result from reduced expression of TGF$\beta$-3 in vivo.

The hypothesis that reduced levels of TGF$\beta$-3 may allow bone loss is undermined by the findings that TGF$\beta$ has been isolated from a large number of sources and exhibits widely divergent effects. For example, it inhibits the growth of mesenchymal cells and epithelial cells, it induces biosynthesis of proteoglycans, fibronectins and plasminogen activator and is chemotactic for fibroblasts, macrophages and smooth muscle cells. See, Flaumenhaft et al., 1993, J. Cell. Bio. 120(4): 995–1002.

Furthermore, antiestrogens such as tamoxifen or toremifene induce human fetal fibroblasts to secrete TGF$\beta$ (without reference to isoform) in the absence of estrogen receptor. Colletta et al., 1990, Br. J. Cancer 62: 405–409. TGF$\beta$ has been found to stimulate osteoblastic bone formation and to inhibit osteoclast formation and osteoclast activities. Mundy, 1991, Clinical Application of TGF$\beta$, Ciba Foundation Symposium No. 157: 137–151, Wiley, Chichester. TGF$\beta$ repressed division of one human endometrial cancer cell line (Ishikawa), but was shown to be mitogenic with respect to another such cell line (HEC-50). Murphy et al., 1992, J. Ster. Biochem. Molec. Bio. 41: 309–314.

Three months of antiestrogen treatment with tamoxifen has been correlated with induction of extracellular TGF$\beta$-1 in breast cancer biopsies. Butta et al., 1992, Cancer Res. 52: 4261–4264. Decreased concentrations of TGF$\beta$-1 mRNA were found in one human endometrial cancer cell line (HEC-50) grown in media containing 1% ctFBS (twice charcoal stripped FBS) when such cells were exposed to either estradiol or certain antiestrogens. Gong et al., 1992, Canc. Res. 52: 1704–1709.

TGF$\beta$-2 mRNA is expressed by the T-47D and MDA-MB-231 cell lines. Treatment of these cell lines with estradiol reduced TGF$\beta$-2 mRNA expression, but tamoxifen did not exhibit the same effect. TGF$\beta$-3 induces mitogenesis, collagen synthesis and alkaline phosphatase activity in osteoblast enriched bone cell cultures at a three to five fold higher rate than TGF$\beta$-1. Arrick et al., 1990, Canc. Res. 50: 299–303.

A general review of the properties of TGF$\beta$ was set forth in Sporn et al., 1987, J. Cell Bio. 105: 1039–1045; Massague, 1987, Cell 49: 437–438; and Moses, 1990, Cell 63: 245–247 (1990). These references generally describe the properties exerted by TGF$\beta$ in in vitro and in vivo systems.

E. Regulatory Elements

The complex pattern of expression described above suggests a unique and complex mechanism of regulation of expression of the various TGF$\beta$ isoforms. The promoter regions for each of the genes TGF$\beta$-1, TGF$\beta$-2 and TGF$\beta$-3 have been cloned and described. Kim et al., 1989, J. Biol. Chem. 264: 402–408; Noma et al., 1991, Growth Factors, 4: 247–255; Lafyatis, et al., 1990, J. Biol. Chem. 265: 19128–19136.

The promoters for TGF$\beta$-2 and TGF$\beta$-3 have been characterized and have been reported to contain cAMP responsive elements, AP-1 sites, AP-2 sites and SP-1 sites. The Noma reference indicates that the TGF$\beta$-2 promoter activity was dependent upon both upon the region of the promoter investigated and the cell line selected for the induction assay.

F. Serum Lipids

As described above, osteoporosis is clearly one of the most debilitating effects engendered in women who exhibit reduced levels of estrogen production. Another notable health concern experienced by such women is elevated serum levels of low density lipoproteins. High concentrations of LDLs are correlated with increased incidence of coronary artery disease, atherosclerosis and myocardial infarction.

LDL receptors in the liver recruit both LDL and intermediate density lipoprotein from plasma, and are thought to thus lower serum lipid concentrations. Ma et al., 1986, Proc. Natl. Acad. Sci. USA 83: 792-796. Antiestrogens, such as tamoxifen, are known to reduce serum concentration of LDLs. Love et al., 1991, Annals of Intern. Med. 115:860-864. From these data, a hypothesis can be drawn that the mechanism of TGFβ-3 regulation and LDLR regulation may show some similarities.

G. Other Screening Methods

At least one method for efficiently screening the biological activity of a large number of compounds is set forth in International Patent Application No. PCT/US92/00419, which claims methods for transcriptionally regulating the expression of a growth factor. This patent discloses assays to identify compounds capable of inducing transcription via the promoter regions of the human growth hormone gene, the c-ErbB2 gene, the promoter region of the K-ras sequence and the early promoter and enhancers of cytomegalovirus. This application is directed primarily towards the problem of determining the regulation of various oncogenes.

To date, identifying compounds that are likely to display an anti-osteoporotic effect or a serum lipid lowering effect has required virtually random investigation of individual compounds on the basis of epidemiological studies, the utility of related chemical compounds in achieving the desired effect and other time consuming and inefficient methods. Both the delay caused by the current screening methods and the economic costs of such inefficient testing emphasize the need for economical and efficient methods for identifying potential anti-osteoporotic drugs and potential serum lipid lowering drugs worthy of additional investigation.

BRIEF DESCRIPTION OF THE DRAWINGS

FIG. 1 depicts the promoter region of the TGFβ-1 gene (SEQ ID No.: 1).

FIG. 3 depicts the promoter region of the TGFβ-3 gene (SEQ ID No.: 3).

FIG. 4 depicts the relative levels of expression of reporter gene in cells transfected with expression constructs comprising the TGFβ-1 promoter operably linked to the CAT gene, the TGFβ-2 promoter operably linked to the CAT gene, or the TGFβ-3 promoter operably linked to the CAT gene, in the presence of a control compound, estrogen, raloxifene and tamoxifen. In general, the TGFβ-3 construct containing-cells express the highest levels of reporter gene, followed by those containing the TGFβ-2 construct and the TGFβ-1 construct.

FIG. 7 depicts the various domains of ER protein expressed by the deletion constructs set forth in Example XI. Additionally, the relative fold induction achievable in cells transfected with the various mutant ERs and an expression construct comprising the TGFβ-3 promoter and the luciferase gene are shown.

SUMMARY OF THE INVENTION

Figure 2B:
FIG. 2 depicts the promoter region of the TGFβ-2 gene (SEQ ID No.: 2, position 60-3726).

The present invention relates to novel and efficient methods of screening chemical compounds to determine whether those compounds are capable of modulating steroid hormone-responsive gene expression from a mammalian promoter comprising a raloxifene responsive element as discovered and described herein. The invention comprises nucleic acids consisting essentially of the nucleotide sequence of a mammalian promoter comprising such a raloxifene responsive element. In a preferred embodiment, the promoter comprising the raloxifene responsive element is derived from the promoter region of the gene for human $TGF\beta$-3 or $TGF\beta$-2.

The invention further comprises recombinant eukaryotic expression constructs comprising a promoter having a raloxifene responsive element that is operably linked to a reporter gene. In preferred embodiments, the reporter gene is the chloramphenicol acetyltransferase gene or the luciferase gene. Particularly, preferred is the luceferase gene. Cells transfected with such eukaryotic expression constructs that are capable of expressing the reporter gene when such cells are exposed to raloxifene or other anti-estrogenic compounds are also provided by the invention.

In the first aspect, the invention provides a nucleic acid consisting essentially of a nucleotide sequence comprising a raloxifene responsive element, where the element is isolated from the promoter region of a mammalian, preferably human, transforming growth factor $\beta$ gene. In preferred embodiments, the transforming growth factor $\beta$ gene is the human $TGF\beta$-2 gene or the human $TGF\beta$-3 gene. In further preferred embodiments of this aspect of the invention, the nucleic acid consists essentially of promoter sequences of the $TGF\beta$-3 gene as described in plasmids pB-301 (containing $TGF\beta$-3 promoter sequences from positions $-301$ to $+110$); pB-221 (containing $TGF\beta$-3 promoter sequences from positions $-221$ to $+110$); pB-91 (containing $TGF\beta$-3 promoter sequences from positions $-91$ to $+110$); pB-60 (containing $TGF\beta$-3 promoter sequence from positions $-60$ to $+110$); pB-47 (containing $TGF\beta$-3 promoter sequence from positions $-47$ to $+110$) and pB-38 (containing $TGF\beta$-3 promoter sequence from positions $-38$ to $+110$), as further described herein.

In a second aspect, the invention provides a recombinant expression construct comprising a nucleic acid consisting essentially of a nucleotide sequence comprising a raloxifene responsive element, where the element is isolated from the promoter region of a mammalian, preferably human, transforming growth factor $\beta$ gene, operably linked to a reporter gene. In preferred embodiments, the transforming growth factor $\beta$ gene is the human $TGF\beta$-2 gene or the human $TGF\beta$-3 gene. In preferred embodiments, the reporter gene is the chloramphenicol acetyltransferase gene or the luciferase gene. Particularly, preferred is the luciferase gene. In further preferred embodiments of this aspect of the invention, the nucleic acid comprises a promoter sequence consisting essentially of the promoter sequences of the $TGF\beta$-3 gene comprising the plasmids pB-301 (containing $TGF\beta$-3 promoter sequence from positions $-301$ to $+110$); pB-221 (containing $TGF\beta$-3 promoter sequences from positions $-221$ to $+110$); pB-91 (containing $TGF\beta$-3 promoter sequences from positions $-91$ to $+110$); pB-60 (containing $TGF\beta$-3 promoter sequences from positions $-60$ to $+110$); pB-47 (containing $TGF\beta$-3 promoter sequence from positions $-47$ to $+110$) and pB-38 (containing $TGF\beta$-3 promoter sequence from positions $-38$ to $+110$), as further described herein and operably linked to a reporter gene.

In another aspect, the recombinant expression constructs of the invention are capable of expressing the reporter gene encoded by such a construct in eukaryotic cells transfected with such a construct. In preferred embodiments, such eukaryotic cells additionally express an estrogen receptor protein or mutant derivative thereof. In particularly preferred embodiments, expression of the reporter gene by the recombinant expression constructs of the invention is capable of being induced by treatment of such cells with raloxifene or other anti-estrogenic compounds as defined herein.

A third aspect of the invention provides a eukaryotic cell into which has been introduced a recombinant expression construct of the invention. In a preferred embodiment, the eukaryotic cell is a cell transfected with a recombinant expression construct of the invention. In a preferred embodiment, the eukaryotic cells of the invention express an estrogen receptor protein or mutant derivative thereof. In particularly preferred embodiments, expression of the reporter gene in such cells is capable of being induced by treatment of such cells with raloxifene or other anti-estrogenic compounds as defined herein.

The invention also provides methods for screening a multiplicity of compounds to identify those compounds having potential as anti-osteoporotic agents.

In one aspect of this embodiment of the invention is provided a method for screening a multiplicity of compounds to identify compounds having potential as anti-osteoporosis agents. The method provided by this aspect of the invention comprises identifying a compound of the multiplicity that is capable of inducing transcription from a raloxifene-responsive element of a mammalian promoter, that is not a non-specific transcription inducer, is not capable of inducing transcription from an estrogen-responsive element of a mammalian promoter and that is an anti-estrogenic or non-estrogenic compound. The method provided by this embodiment further comprises the steps of (a) assaying for the ability of the compound to induce transcription from a raloxifene responsive element of a mammalian promoter; (b) assaying for the inability of the compound to induce transcription from a mammalian promoter not having a raloxifene responsive element; (c) assaying for the inability of the compound to induce transcription from an estrogen responsive promoter; and (d) assaying for the ability of the compound to inhibit estrogen induction of transcription from an estrogen responsive promoter in the presence of estrogen.

In a preferred embodiment, the assay of subpart (a) comprises the step of determining the ability of the compound to induce expression of a reporter gene operably linked to the mammalian promoter comprising a raloxifene responsive element. In another preferred embodiment, the assay of subpart (b) comprises the step of determining the inability of the compound to induce expression of a reporter gene operably linked to the mammalian promoter wherein the promoter is not comprised of a raloxifene-responsive element. Another preferred embodiment of this aspect of the invention provides the assay of subpart (c) comprising the step of determining the inability of the compound to induce expression of a reporter gene operably linked to an estrogen responsive mammalian promoter. In a final preferred embodiment, the invention provides the assay of subpart (d) comprising the step of determining the ability of the compound to inhibit estrogen-dependent induction of expression of a reporter gene operably linked to an estrogen responsive mammalian promoter in the presence of estrogen.

In particularly preferred embodiments of this aspect of the invention, the raloxifene responsive mammalian promoter is isolated from a mammalian, preferably human, transforming growth factor $\beta$ gene. Most preferred are embodiments wherein the transforming growth factor $\beta$ gene is the human TGF$\beta$-2 gene or the human TGF$\beta$-3 gene. In other preferred embodiments, the reporter gene is the chloramphenicol acetyltransferase gene or the luciferase gene. In further preferred embodiments of this aspect of the invention, the raloxifene responsive promoter sequences consisting essentially of the promoter sequences of the TGF$\beta$-3 gene comprising the plasmids pB-301 (containing TGF$\beta$-3 promoter sequences from positions −301 to +110); pB-221 (containing TGF$\beta$-3 promoter sequences from positions −221 to +110); pB-91 (containing TGF$\beta$-3 promoter sequences from positions −91 to +110); pB-60 (containing TGF$\beta$-3 promoter sequences from positions −60 to +110); pB-47 (containing TGF$\beta$-3 promoter sequences from positions −47 to +110) and pB-38 (containing TGF$\beta$-3 promoter sequences from positions −38 to +110), as further described herein and operably linked to a reporter gene.

Specific preferred embodiments of the present invention will become evident from the following more detailed description of certain preferred embodiments and the claims.

DETAILED DESCRIPTION OF THE PREFERRED EMBODIMENTS

This specification contains a number of abbreviations. As used herein, TGF$\beta$ shall mean transforming growth factor $\beta$ (without reference to isoform). TGF$\beta$-1, TGF$\beta$-2 and TGF$\beta$-3 shall have the meanings well-established in this art, i.e., to represent the three known isoforms of transforming growth factors $\beta$ genes. As used herein, the abbreviation CAT shall be taken to mean chloramphenicol acetyl CoA transferase. "Estradiol" is an estrogen and, at times, is abbreviated herein as E2.

The term "raloxifene responsive element" as used herein refers to nucleotide sequences of the nucleic acid comprising a mammalian promoter that are capable of inducing transcription of any structural gene to which the raloxifene responsive element is operably linked in host cells that are exposed to raloxifene. Raloxifene responsive elements include, but are not limited to the nucleotide sequences comprising the TGF$\beta$ promoter sequences of the plasmids pB-301 (containing TGF$\beta$-3 promoter sequences from positions −301 to +110); pB-221 (containing TGF$\beta$-3 promoter sequences from positions −221 to +110); pB-91 (containing TGF$\beta$-3 promoter sequences from positions −91 to +110); pB-60 (containing TGF$\beta$-3 promoter sequences from positions −60 to +110); pB-47 (containing TGF$\beta$-3 promoter sequences from positions −47 to +110) and pB-38 (containing TGF$\beta$-3 promoter sequences from positions −38 to +110), as further described herein, and nucleic acids having substantially the same biological activity as those nucleic acids. This definition is intended to encompass natural allelic variations in the promoter regions of the TGF$\beta$ genes. Isolated raloxifene responsive elements of the present invention may be derived from TGF$\beta$ promoters of any mammalian species of origin, but are preferably of human origin.

As used herein, anti-estrogens will be taken to include full and partial antagonists of estrogen. All estradiols used in the Examples described herein are 17$\beta$-estradiol.

All portions of promoter sequences are identified in terms of their distance, in number of nucleotides, from the major transcriptional start site of the gene, taking this start site to be +1 as shown in FIGS. 1–3. A negative sign (−) preceding the number indicates the nucleotide is 5′ to the start site, a positive sign (+) preceding the number indicates the nucleotide is 3′ to the start site. The sequences are also identified by the numbering indicated in SEQ ID NOS:1–3, and are specifically correlated with numbering of FIGS. 1–3.

DNA that encodes the raloxifene responsive elements of the present invention may be obtained, in view of the instant disclosure, by chemical synthesis, by in vitro amplification [including but not limited to the polymerase chain reaction (PCR)], or by combinations of these procedures from naturally-occurring sources, such as cultures of mammalian cells, genomic DNA from such cells or libraries of such DNA.

The present inventive raloxifene responsive elements may be advantageously operably linked to reporter genes and used to either transiently or stably transform appropriate host cells through the use of appropriate vectors, constructs and means well known in the art, such as DNA mediated gene transfer means including but not limited to transfection, electroporation and virally-mediated infection. The term "recombinant expression construct" as used herein is intended to mean DNA constructs capable of directing the expression of reporter genes to which the raloxifene responsive elements of the invention are operably linked.

DNA regions are operably linked when they are functionally related to each other. For example, a promoter is operably linked to a coding sequence if it controls the transcription of the sequence; a ribosome binding site is operably linked to a coding sequence if it is positioned so as to permit translation. Generally, operably linked means contiguous.

Reporter genes are genes that encode structural proteins capable of quantification by standard means such as measuring enzymatic activity, colorimetry, chemiluminescence, the presence of radioactivity in a sample, ELISA, antibody binding, radioimmunoassay or other methods of quantification known to those in the art. The reporter gene used will vary depending upon the host selected and the transformation method chosen. Useful reporter genes include but are not limited to chloramphenicol acetyltransferase, luciferase, β-galactosidase, alkaline phosphatase or any other quantifiable protein product. In a preferred embodiment of the invention, the reporter gene is luciferase.

Transfected cells are cells that have been transfected with raloxifene responsive element-reporter gene recombinant expression constructs made using recombinant DNA techniques. Cells that have been transfected with recombinant raloxifene responsive element-reporter gene expression constructs that express the estrogen receptor, either as a characteristic of such cells or due to the cotransfection of an estrogen receptor encoding expression construct, will express the gene product of the reporter gene under appropriate circumstances (i.e., exposure to an anti-estrogen or other inducer). For example, a preferred cell line appropriate for use in the present invention, MCF-7, constitutively expresses the estrogen receptor. For such cell lines, transfection with the recombinant raloxifene responsive element-reporter gene expression constructs alone will yield cells appropriate for use in the present invention. Alternatively, MG63 cells express reporter genes in a raloxifene-dependent manner, only upon cotransfection of a raloxyene responsive element-reporter gene expression construct and an estrogen receptor expression construct.

Cultures of cells derived from multicellular organisms are desirable hosts for expression of the raloxifene responsive element-reporter gene expression construct. In principle, any higher eukaryotic cell culture that either naturally expresses the estrogen receptor, or that has been genetically modified to express the estrogen receptor [(or part of that receptor)] is useable. Mammalian cells are preferred, as illustrated in the Examples. Propagation of such cells in cell culture has become a routine procedure. See *Tissue Culture*, Academic Press, Kruse & Patterson, editors (1973). Examples of useful host cell lines are MCF-7, MG63, HeLa, RL95.2, HepG2 and CHO cells (all available from the American Type Culture Collection, Rockville, Md.). For the purposes of the present invention, use of the MCF-7 cell line is particularly preferred, as this cell line constitutively expresses estrogen receptor.

Host cells that express the estrogen receptor or part of that receptor and contain a raloxifene responsive element-reporter gene expression construct can be used to evaluate compounds for their ability to induce transcription via the raloxifene responsive element as described in the Examples infra. In a preferred embodiment of the invention, compounds will be considered to induce transcription via a regulatory element (including but not limited to nucleic acid derived from a TGFβ promoter or deletion construct thereof) if transcription of the reporter gene is increased twofold in the presence of the compound compared with expression in the absence of the compound. In a less preferred embodiment, compounds will be considered to be transcriptional inducers if they induce transcription to a level fifty percent above that of the control. In general, however, induction detectably above background is adequate to show induction by a chemical compound.

In the practice of the aspects of the invention embodying screening methods (see Example XIII), use of the plasmid pB-301 is preferred due to the high level of responsiveness to raloxifene exhibited by this plasmid. Other embodiments utilize constructs containing the TGFβ-3 promoter region encompassing positions −38 to +75. In all operative embodiments of the invention, the raloxifene responsive element is operably linked to a reporter gene in a context allowing transcription, as this element is necessary to allow the raloxifene responsive induction described herein.

The order of carrying out the steps of the screening methods of the invention may be varied, and in some instances, some of the steps may be omitted. The Examples that follow are illustrative of specific embodiments of the invention, and various uses thereof. They are set forth for explanatory purposes only, and are not to be taken as limiting the invention.

EXAMPLE I

Construction of Reporter Plasmids

A. phTG12, pTGF-1 and pB-499

As a first step in developing cell lines useful in screening potential anti-osteoporotic agents, a series of reporter plasmids encoding the chloramphenicol acetyltransferase gene (CAT; Gorman et al., 1982, Molec. Cell. Biol. 2: 1044–1051) operably linked to promoter sequences from the TGFβ-1, TGFβ-2 and TGFβ-3 genes were obtained from A. Roberts, National Institutes of Health, Laboratory of Chemoprevention (NIH/NCI, Bethesda, Md.). These plasmids were designated phTG12 (TGFβ-1), pTGF-1 (TGFβ-2) and pB-499 (TGFβ-3), respectively. The sequences for each of these promoters can be found in Kim et al., 1989, J. Biol. Chem. 264: 402–408 (TGFβ-1); Noma et al., 1991, Growth Factor 4: 247–255 (TGFβ-2) and Lafyatis et al., 1990, J. Biol. Chem. 265:19128–19136 (TGFβ-3). (The promoter sequence of the TGFβ-1 gene has been submitted to GenBank/EMBL Data Bank under accession number J04431). The TGFβ-1, TGFβ-2 and TGFβ-3 promoter sequences are shown in FIGS. 1, 2 and 3, respectively, and as SEQ ID NOS: 1, 2 and 3, respectively.

Alternatively, CAT-containing reporter plasmids operably linked to each of the TGFβ promoter sequences can be produced by subcloning each TGFβ promoter into a commercially-available CAT construct (for example, pCAT-Basic, Promega, Madison, Wis.) using conventional cloning techniques (see Sambrook et al., 1990, *Molecular Cloning: A Laboratory Manual*, 2d ed., Cold Spring Harbor Press: Cold Spring Harbor, N.Y.).

In order to identify region(s) of the TGFβ-3 gene promoter responsive to the antiestrogen raloxifene, CAT reporter gene expression directed by constructs containing partial sequences of the TGFβ-3 gene promoter were analyzed. Six TGFβ-3 promoter deletion/CAT reporter constructs were obtained from A. Roberts. Plasmid designations and the extent of the promoter region contained in each of these plasmids are set forth below:

| | | |
|---|---|---|
| PB-301 | −301 to +110 | (corresponding to 1896 to 2306 shown in FIG. 3 and SEQ ID NO: 3) |
| pB-221 | −221 to +110 | (corresponding to 1976 to 2306 shown in FIG. 3 and SEQ ID NO: 3) |
| pB-91 | −91 to +110 | (corresponding to 2106 to 2306 shown in FIG. 3 and SEQ ID NO: 3) |
| pB-60 | −60 to +110 | (corresponding to 2137 to 2306 shown in FIG. 3 and SEQ ID NO: 3) |
| pB-47 | −47 to +110 | (corresponding to 2150 to 2306 shown in FIG. 3 and SEQ ID |

| | | |
|---|---|---|
| pB-38 | −38 to +110 | NO: 3)<br>(corresponding to 2159 to 2306 shown in FIG. 3 and SEQ ID NO: 3) |

Two additional TGFβ-3 promoter deletion constructs were constructed as described below. The first of these consisted of human TGFβ-3 promoter region sequences corresponding to positions −38 to +75 in the promoter sequence (corresponding to 2159 to 2271 shown in FIG. 3 and SEQ ID NO:3) (see Lafyatis et al., ibid.). The second promoter deletion construct consisted of human TGFβ-3 promoter region sequences corresponding to positions −38 to +35 in the promoter sequence (corresponding to 2159 to 2231 shown in FIG. 3 and SEQ ID NO:3). (The well-established practice in this art is to identify all promoter sequences identified with respect to the distance from the transcription start site).

These plasmids were generated as follows. Oligonucleotides corresponding to the extent of the TGFβ-3 promoter sequence desired in each plasmid were synthesized using a DNA/RNA synthesizer (Model 394, Applied Biosystems Inc., Foster City, Calif.) under β-cyanoethyl phosphoamidite synthesis conditions specified by the manufacturer. Complementary pairs of oligonucleotides for each plasmid construct were synthesized, purified, mixed and allowed to anneal to form double-stranded DNA corresponding to the appropriate TGFβ-3 promoter sequences using conventional methods (Sambrook et al., ibid.). HindIII and XbaI restriction enzyme recognition sites were synthesized as the appropriate overhanging ends at the 5′ and 3′ ends of the sequences, respectively. Double-stranded promoter sequences were then ligated into the HindIII/XbaI-digested CAT reporter plasmid pB-301 and propagated in bacteria under standard conditions. The reporter plasmid produced in this way that contained the −38 to +75 region of the TGFβ-3 promoter was termed pTGFβ+75CAT, and the plasmid that contained the −38 to +75 region of the TGFβ-3 promoter was termed pTGFβ+35CAT. These plasmids were used in CAT assays as described below in Example V.

B. Luciferase reporter plasmids containing TGFβ-3 promoter deletion constructs, including control containing no portion of the promoter region: pTGFβ-301LUC, pTGFβ-38LUC, pTGFβ+75LUC, pTGFβ+35LUC and pLUC Four plasmids were constructed containing the luciferase gene (REF) expressed under the transcriptional control of TGFβ-3 promoter sequences and varying deletion derivatives thereof. The plasmid pTGFβ-301LUC was made by digesting pB-301 with HindIII and thereafter the ends of the HindIII digestion-generated overhang were blunted by treatment with the Klenow fragment of bacterial DNA polymerase I (Boehringer-Mannheim, Indianapolis, IN). XbaI digestion was then performed to liberate the portion of the TGFβ-3 promoter corresponding to positions −301 to +110. This fragment was subcloned into SmaI/XbaI-digested pSP73 (Promega) to generate the shuttle vector pSPTGFβ-301.

After in vivo amplification in bacteria, a preparation of isolated and purified pSTTGFβ-301 was digested with NdeI and HindIII, and the promoter sequence-containing fragment isolated after separation on a 0.8% agarose gel (BRL-LifeTechnologies, Inc., Gaithersburg, Md). The luciferase-containing construct pLDLRLUC10 (as described in U.S. patent application Ser. No. 08/018,985, filed Mar. 3, 1993 and further described in Section C., below) was NdeI/HindIII-digested and purified after agarose gel electrophoresis. These isolated fragments were then mixed, ligated and used to transform bacteria (Sambrook et al., ibid.).

The plasmids pTGFβ-38LUC, pTGFβ+75LUC and pTGFβ+35LUC were made by first excising the TGFβ-3 promoter sequences from pB-38, pTGFβ+75CAT and pTGFβ+35CAT, respectively, by BamHI/XbaI double digestion. The luciferase-containing plasmid pGL2-Basic (or "pGL2LUC") (Promega) was prepared by NheI/BamHI digestion, and each of the recombinant plasmids made by ligation of the appropriate TGFβ-3 promoter sequences into the luciferase-containing plasmid. These plasmids were used in luciferase assays as described below in Example VI.

A control plasmid containing the luciferase gene but harboring no portion of the TGFβ-3 gene was constructed by digesting pTGFβ+75LUC plasmid DNA with restriction endonuclease XbaI and HindIII. Protruding ends were filled by Klenow enzyme reaction in the presence of all four dNTPS under standard conditions (Sambrook et al., ibid.). The ends thus blunted were ligated with T4 DNA ligase (Boehringer Mannheim) under manufacturer suggested conditions. The resulting plasmid was designated pLUC.

C. LDLR Promoter Containing Reporter Plasmid: pLDLRLUC10

The plasmid pLDLRLUC10 was described in U.S. patent application. Ser. No. 08/018,985, filed Mar. 3, 1993 (hereinafter, the '985 application). The construction of this plasmid is described in detail as follows:

A 1546 base pair sequence of the human LDL receptor promoter was amplified using the polymerase chain reaction. A reaction mixture containing 20 picomoles each of the synthetic oligonucleotides:

5′-GCGCCATATGAGTCTTAACTG-CCAAAAATTCTTATCATCAAT-3′ (SEQ ID NO:4)

and

5′-AAGCAAGCTTTCGCAGCCTCTGCCAGG-CAGTGTCCCGACCCGGA-3′ (SEQ ID NO:5)

and 1 μg human genomic DNA purified from the adenocarcinoma cell line P3UCLA, 200 μM each of dATP, dGTP, dCTP and TTP, 2.5 units of Taq DNA polymerase, 10 mMTris-HCl pH 9.3, 50 mM KCl, 15 mMMgCl₂, 0.1% gelatin in a final volume of 100 μL was subjected to 30 cycles consisting of 15 sec at 96° C., 30 sec at 55° C., and 1 min at 72° C. The material was subject to gel electrophoresis on a 1% agarose gel and a 1546 basepair (bp) band isolated and restriction enzyme digested with HindIII and NdeI. This fragment was ligated into the plasmid pSP72 (Promega), which had previously been digested with HindIII and NdeI. The resulting vector, pNLDLRP, was digested with NdeI and HindIII, the material was electrophoresed on a 1% agarose gel and the 1546 base pair LDL receptor sequence reisolated therefrom.

Plasmid vector pSv2 was constructed by digesting plasmid pSv2-globin with HindIII and BglII then ligating an NruI-XhoI linker into the vector. Plasmid pSv2 globin is disclosed in U.S. Pat. No. 4,775,624, the entire teaching of which is herein incorporated by reference. The linker contained the following sequences:

5'-AGCTTCGCGACTCGAGA-3' (SEQ ID NO:6) and
5'-GATCTCTCCAGTCGCGA-3' (SEQ ID NO:7).

The resulting vector was designated pSv2-H NXB because it contained a BamHI site, an NruI site, an XhoI site and a BglII site. The HindIII-BglII fragment of plasmid pAlc4(NRRL B-18783), which contains the firefly luciferase gene (REF), was then ligated into the HindIII-BglII site of plasmid pSv2-HNXB.

The 1546 base pair fragment described above was isolated and cloned into the vector pSv2 containing firefly luciferase reporter gene that had been restriction enzyme digested to completion with NdeI and partially with HindIII. The resulting vector, pLDLRLUC10 contains the human LDL receptor promoter directing expression of the firefly luciferase gene, an ampicillin resistance marker and an origin of replication.

EXAMPLE II

Human Estrogen Receptor Expression Plasmids

The estrogen receptor-containing mammalian expression constructs pCMVER and pRSV-ER (described in detail in Reese & Katzenellenbogen, 1990, J. Biol. Chem. 266: 10880–10887) were obtained from B. S. Katzenellenbogen, Department of Physiology and Biophysics, University of Illinois (Urbana-Champaign, Ill.). These plasmids were used in expression assays as described below, for example, in Example VII.

EXAMPLE III

Construction of An Estrogen Responsive Element/Luciferase Gene-Containing Plasmid Complementary oligonucleotides corresponding to the estrogen-responsive element (ERE) from the Xenopus laevis vitellogenin Az gene promoter (corresponding to positions −341 to −310; Metzger et al., 1988, Nature 334: 31–36) were designed, synthesized and annealed to form a double-stranded region that is an estrogen responsive element essentially as described in Example I. A sequence comprising an XhoI restriction enzyme recognition site was synthesized to be flanking the ERE sequences, the element having the following nucleotide sequence (shown as SEQ ID NOS:8 and 9, respectively):

5'-TCG-AGA-AAA-GTC-AGG-TCA-CAG-TGA-CCT-GAT-CAA-AC-3'    3'-CT-TTT-CAG-TCC-AGT-GTC-ACT-GGA-CTA-GTT-TGA-GCT-5'

The double-stranded ERE was subcloned into XhoI-digested pGL12-Basic (Promega) whereby the luciferase gene was placed under the transcriptional influence of the ERE. This plasmid was designated pGL2ERELUC and used in further experiments as described below (Example VI).

EXAMPLE IV

DNA Transfection

A. Cell culture

Mammalian cells were cultured in media (termed 3:1 media) consisting of Dulbecco's modified Eagle's media and F12 media (mixed in a ratio of 3:1, obtained from GIBCO, Grand Island, N.Y.), without phenol red, containing 10% fetal bovine serum (FBS; Hyclone, Logan, Utah). Cells were passaged at 4 day intervals. One day prior to transfection, cells were trypsinized by incubating them with 1 mL of a solution of 0.05% trypsin/5.3 mM tetrasodium ethylenediamine tetraacetate (GIBCO) for 5 min at room temperature and then seeded in 3:1 media containing 10% charcoal-stripped FBS (csFBS; Hyclone) at densities of one million cells per 10 cm culture dish.

Transient co-transfection of TGFβ constructs and human ER constructs

Co-transfection experiments were performed in MG63 (human osteosarcoma) cells, using the ProFection Mammalian Transfection System (Promega). Ten μg of TGFβ promoter-containing reporter plasmid DNA and 5 μg of human estrogen receptor (hER)-containing expression plasmid (pRSV-ER or pCMV-ER; described in detail in Reese & Katzenellenbogen, 1990, J. Biol. Chem. 266: 10880–10887 and obtained from B. S. Katzenellenbogen, Department of Physiology and Biophysics, University of Illinois (Urbana-Champaign, Ill.) or pRSV (control) plasmid were mixed, co-precipitated and transfected into 2–4 million cells in 10 cm culture dishes. After incubating the cells with the DNA precipitate at 37° C. for 15 h, the DNA precipitate was removed by twice washing the cells with Dulbecco's phosphate buffered saline (D-PBS; GIBCO). The cells were then refed with fresh 3:1 media containing 10% csFBS. Compounds to be evaluated for their ability to modulate reporter gene expression were added at the appropriate times and assayed as described below.

C. Stable co-transfection of TGFβ constructs and human ER constructs

MCF-7 cells were used for transfection experiments resulting in stable integration of transfected plasmid sequences into the recipient cell genome. In these experiments, TGFβ promoter containing plasmid DNA was mixed with DNA encoding a selectable marker. For example, 60 μg of TGFβ promoter-containing plasmid DNA (pTGFβ-301LUC, pGL2LUC or pGL2ERELUC) were mixed with 60 μg of the pSV2HYG-derivative, hygromycin resistance gene-containing plasmid pSV2HYGtB (further described in U.S. patent application Ser. No. 07/953,633, filed Sep. 29, 1992, hereby incorporated by reference), and transfected onto 2 million MCF-7 cells using the ProFection system as described above (Promega). After overnight incubation at 37° C., the precipitate was washed from the cells as described above and the cells then refed with fresh 3:1 media containing 10% FBS and cultured for an additional 48 h at 37° C. at which time the cells had typically reached confluency. Cells were trypsinized as described above and each culture dish replated into two 10 cm culture dishes in 3:1 media containing 10% FBS. Hygromycin resistance was selected by culturing the cells in media supplemented with 200 μg/mL hygromycin B (Calbiochem-Novabiochem, LaJolla, Calif.). This selective media was replaced with fresh hygromycin B-supplemented media every 2 days without disturbing the cells for the duration of the selection experiment. Clonal colonies became visible after growth for approximately 14 days in selective media. Such clones were isolated and transferred to individual wells of 24-well cell culture dishes (Flow Laboratories, McLean, Va.) using a sterile pipette tip. Such clones were grown and maintained in selective media.

To identify hygromycin-resistant clones that had been successfully co-transfected with luciferase gene-containing plasmid sequences, the polymerase chain reaction (PCR) was used to detect luciferase cDNA-derived DNA sequences in transfectant DNA. Oligonucleotide PCR primers were synthesized corresponding to positions 355–373 (sense primer) and 929–911 (antisense primer) of the luciferase cDNA sequence. PCR was performed using Perkin-Elmer GeneAmp PCR System 9600 for 35 cycles under conditions essentially as described by the manufacturer; each PCR cycle included 45 sec at 94° C., 45 sec at 55° C. and two min at 72° C.

Luciferase-containing hygromycin-resistant clones were incubated with estrogen or raloxifene as described above, and the effect on expression of reporter genes analyzed using assays for the amount on enzymatic activity present in cell extracts. For luciferase assays, cells were lysed in eukaryotic cell lysis reagent containing 0.1M phosphate buffer (pH 7.8)/1% TritonX-100 (Boehringer Mannheim)/2 mM EDTA and 1 mM dithiothreitol (DTT; Boehringer Mannheim and assayed using an optimized unenhanced luciferase assay protocol developed by the Analytical Luminescence Laboratory (San Diego, Calif.). Light output was measured and recorded using a microtiter plate luminometer (ML3000, Dynatech Laboratories, Chantilly, Va.). Clones of such cells stably transfected with TGFβ-reporter gene constructs were then used in new antiosteoporotic screening assays as described below (Example XIII).

EXAMPLE V

Analysis of TGFβ Promoter-Mediated Transcriptional Activation by Estrogen and Antiestrogens It was known in the prior art that expression of the TGFβ-1, -2 and -3 genes was differentially inducible using estrogen and tamoxifen (see "Background of the Related Art" above). The extent and pattern of this inducibility was characterized using the TGFβ promoter-containing plasmids described above in a series of in vitro expression assays as follows.

Cultures of MG63 cells were transiently co-transfected with pRSVER plasmid and either phTG12, pTGF-1, or pB2-499 using the ProFection system (Promega). For each transfected cell culture, DNA-containing calcium phosphate precipitates were added dropwise to each culture dish and mixed thoroughly in the media. The pH of the media was carefully maintained between pH 7.2 and pH 7.4. Transfected cell cultures were then incubated overnight in a 5% $CO_2$ atmosphere at 37° C. For all cultures, the precipitate was removed after overnight incubation by aspirating the media from the culture dishes, followed by rinsing each dish twice with D-PBS. For each cotransfected cell line, the buffer was replaced with 10 ml fresh medium containing 10% csFBS and one of the following compositions:

a. 10 μl ethanol (hormone vehicle)=control;
b. 10 μl 17β-estradiol (Sigma) ("estradiol") at a concentration of $10^{-4}$M in ethanol;
c. 10 μl raloxifene (Eli Lilly laboratories) at a concentration of $10^{-4}$M in ethanol;
d. 10 μl Tamoxifen (Sigma) at a concentration of $10^{-4}$M in ethanol.

After 24 h incubation with these hormonal preparations (or the vehicle control), cells were washed twice with D-PBS. The cells were then scraped from the culture dishes using a rubber policeman and 1 ml of D-PBS. Cells were collected by centrifugation at 8,000 rpm for 2 minutes in a tabletop centrifuge (MicroMax Model, IEC, Newark, N.Y.). The supernatant was removed and the cell pellets were resuspended in 150 μL of a 0.25M Tris-HCl solution (pH 7.8). Cells were lysed by three cycles of freezing in a dry ice/ethanol bath and thawing in a water bath at 37° C. water bath (for 3 minutes each cycle). Lysed cell preparations were centrifuged at 15,000 rpm for 5 minutes at 4° C. to remove cell debris. Supernatants containing the soluble cell lysate were transferred to a new set of tubes for assaying chloramphenicol acetyltransferase (CAT) activity.

Before performing CAT assays on such cell lysates, the protein content of each lysate was first determined using a commercially-available assay (BioRad Laboratories, Richmond, Calif.). An amount of each cell lysate containing 100 μg total protein was then mixed with CAT assay buffer (0.4M Tris-HCl (pH 7.8)/ 0.5 mM acetyl-CoA (Boehringer Mannheim)/ 0.1 μCi D-threo-(dichloroacetyl-1,2-[$^{14}$C]-chloramphenicol) for 15 hours. After this incubation, reactions were stopped by vigorously extracting the reaction mixture with 900 μL ethyl acetate. The organic and aqueous phases were separated by brief centrifugation at 14,000 rpm for 1 minute, and approximately 800 μL of the organic phase was transferred to a new set of tubes. Ethyl acetate was evaporated to concentrate the CAT-catalyzed reaction products.

Acetylated and unacetylated chloramphenicol species were resolved by thin layer chromatography using a mixture of 95:5 (v/v) chloroform:methanol as the ascending buffer. Radioactivity from each species so resolved was measured using a Betascope 603 blot analyzer (Betagen, Intelligenetics Inc., Mountain View, Calif.). The percentage of acetylated counts relative to the total counts was calculated to yield relative CAT activities of each transfectant assayed (all CAT activities expressed herein were calculated on this basis). Each assay was performed in duplicate.

A representation of the results of the above experiment for MG63 transfectant cell lines is shown in FIG. [4]. The results of a representative experiment are tabulated below:

TABLE I

| Promoter | Control | Estradiol | | Raloxifene | | Tamoxifen | |
|---|---|---|---|---|---|---|---|
| | | Act. | Fold Ind.† | Act. | Fold Ind. | Act. | Fold Ind. |
| TGFβ-1 | 6.4 | 4.7 | 0.7 | 5.6 | 0.9 | 6.9 | 1.1 |
| TGFβ-2 | 0.8 | 1.29 | 1.6 | 2.3 | 2.9 | 2.0 | 2.6 |
| TGFβ-3 | 0.7 | 2.1 | 2.8 | 5.2 | 7.3 | 1.9 | 2.6 |

† - Fold induction is calculated based on comparison with control

These experiments demonstrate that transcription of the CAT reporter gene is induced by estrogen and the antiestrogens raloxifene and tamoxifen, with raloxifene displaying a greater potency than estrogen, especially for the TGFβ-3 promoter. In contrast, the TGFβ-1 promoter region used in this experiment (positions −1032 to +727) showed no response to either estradiol or raloxifene.

EXAMPLE VI

Differential Induction of TGFβ-3 Promoter and the ERE of the Vitellogenin Promoter by Estrogen and Raloxifene The results obtained in the previous Example demonstrated that the TGFβ-3 gene promoter is transcriptionally responsive to both estrogen and "antiestrogen" compounds such as raloxifene and tamoxifen, and that transcription was induced by raloxifene treatment to a relatively greater degree than the degree of transcriptional induction produced in response to estrogen. This example demonstrates that the gene encoding the Xenopus protein vitellogenin responds in vivo in exactly the opposite fashion, i.e., transcription of the vitellogenin gene is strongly induced by estrogen and only weakly induced by raloxifene. In addition, raloxifene strongly antagonizes estrogen-induced induction of vitellogenin production when the two compounds are given together. The instant results suggested that the TGF$\beta$ promoter sequences directing transcription of the reporter genes in the reporter plasmids assayed above in Example VI contain a novel raloxifene-responsive element, characterized by a unique pattern of estrogen and antiestrogen responsiveness.

This pattern of estrogen and antiestrogen responsiveness was further investigated using the reporter gene assay system described in previous Examples. Cultures of MG63 cells were transiently co-transfected with pB-301 and pRSVER as described in Example IV. Such transiently transfected cultures were tested for transcriptional activation of reporter gene expression by treatment with estradiol and raloxifene at concentrations varying in ten-fold increments from $10^{-9}$M to $10^{-5}$M. The combination of estrogen and raloxifene was also tested by assaying the effects of raloxifene at $10^{-8}$M on reporter gene induction in response to estrogen using the same series of concentrations as with estrogen alone. These assays were performed essentially as in Example V.

Similar assays were performed using cultures of MG63 cells transiently transfected with pGL2ERELUC and pRSVER. In these assays, however, the amount of raloxifene added in combination with estrogen was varied so that the raloxifene concentration was twenty times the concentration of estrogen in the mixture (i.e., $10^{-9}$M estrogen/$2\times10^{-8}$M raloxifene; $10^{-8}$M estrogen/$2\times10^{-7}$M raloxifene, etc.).

Transfected cells were treated with varying amounts and combinations of hormones and then rinsed twice with D-PBS. Cells were then lysed upon incubation with 250 $\mu$L of eukaryotic cell lysis reagent (as described in Example VI) at 4° C. for 20 min and transferred to microcentrifuge tubes by scraping with a rubber policeman. Cell lysates were centrifuged at 14,000 rpm for 1 minute to remove cell debris. Cell extracts (supernatant) were then assayed for protein content and luciferase activities.

Luciferase assays were performed as follows. 50 $\mu$L of each cell extract was added to 100 $\mu$L of reagent A buffer (containing 4.0 mM ATP/15 mM MgSO$_4$/ 30 mM tricine buffer (pH 7.8)/ 10 mM DTT) in individual wells of a microtiter plate. 100 $\mu$L of 1 mM D(−)-luciferin (in 0.1M KPO$_4$ (pH 7.8); Boehringer Mannheim) were added to each well and the amount of light produced measured by using a ML3000 microtiter plate luminometer (under conditions of integrate flash mode, high gain, integrate window=10 seconds, at a temperature of 22° C.). Luciferase activities were calculated as total light output relative to protein content in each cell lysate sample.

The results of these tests are set forth in tabular form below:

TABLE II

| | Control | $10^{-9}$M | $10^{-8}$M | $10^{-7}$M | $10^{-6}$M | $10^{-5}$M |
|---|---|---|---|---|---|---|
| For pB-301 | | | | | | |
| Raloxifene | 0.7 | 2.4 | 9.6 | 9.63 | 9.05 | 5.25 |

TABLE II-continued

| | Control | $10^{-9}$M | $10^{-8}$M | $10^{-7}$M | $10^{-6}$M | $10^{-5}$M |
|---|---|---|---|---|---|---|
| Estradiol | 0.7 | 1.1 | 3.2 | 5.5 | 5.2 | 8.0 |
| E2 + Ral | — | 17.3 | 16.0 | 7.3 | 9.3 | 10.5 |
| For pGL2ERELUC: | | | | | | |
| Raloxifene | 1.7 | 1.9 | 1.5 | 2.0 | 1.9 | 1.9 |
| Estradiol | 1.7 | 5.8 | 5.5 | 5.9 | 6.2 | 6.5 |
| E2 + Ral | — | 1.8 | 1.9 | 2.1 | 2.3 | 2.4 |

Figure 5A:
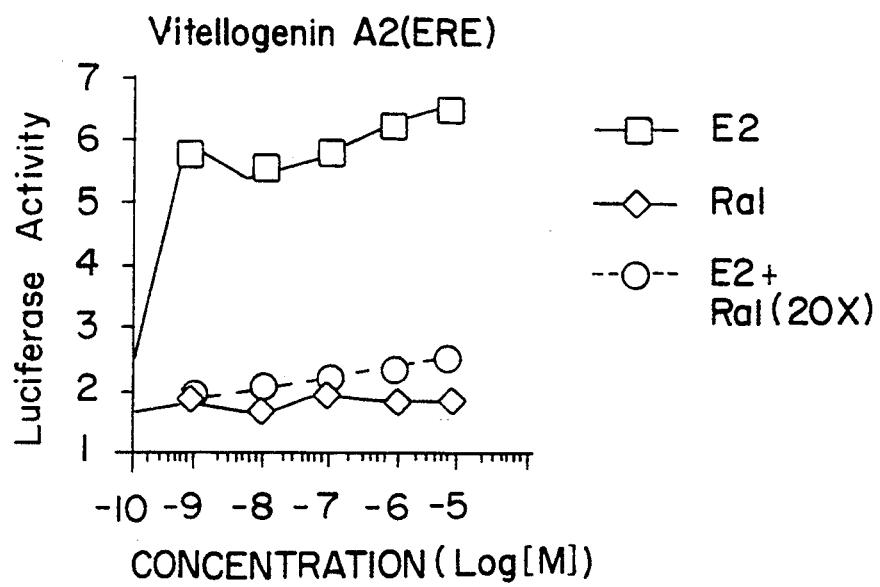
FIG. 5 depicts the induction of a reporter gene under the control of either the estrogen responsive element or a portion of the TGFβ-3 promoter in the presence of estrogen, raloxifene and combinations of estrogen and raloxifene. This figure shows the markedly different patterns of regulation exerted by the two regulatory sequences.
Figure 5B:
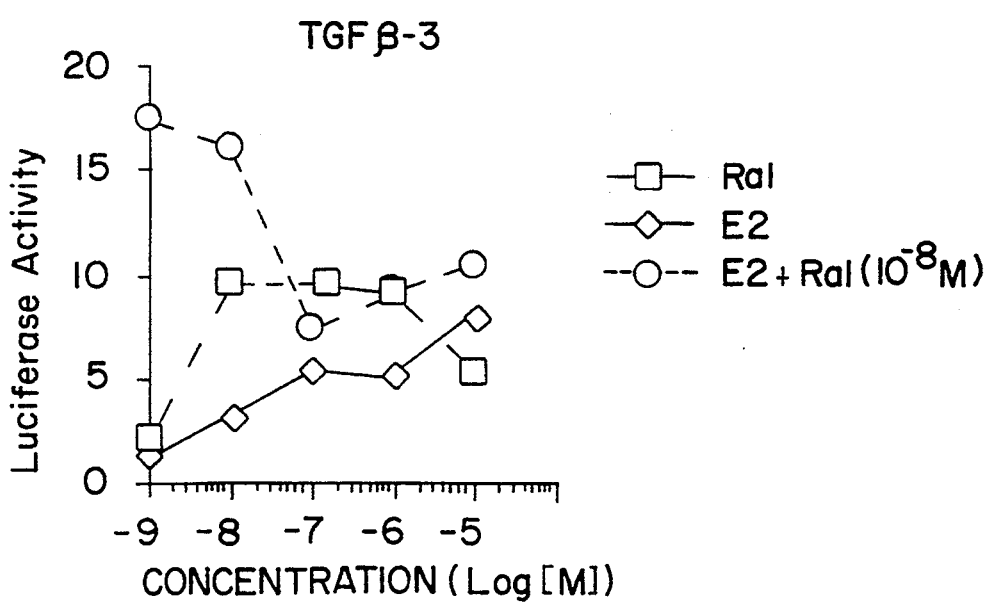

Representative results of these experiments are shown in FIG. 5.

These results clearly demonstrate the existence of a distinct promoter region in the TGF$\beta$ gene promoter that is responsive to antiestrogens. While raloxifene acts as a potent antagonist to transcription initiated by ERE-containing promoters of genes such as the vitellogenin gene, it was found herein to act as a super-agonist in inducing transcription from the TGF$\beta$-3 promoter. Interestingly, at low concentrations, raloxifene and estrogen synergistically induced transcription from the TGF$\beta$-3 promoter in the reporter plasmids of the invention, suggesting that raloxifene-induced gene transcription may be mediated by a novel mechanism.

EXAMPLE VII

Estrogen Receptor Dependent Gene Activation of TGF$\beta$-3 by Estrogen and Antiestrogens It was known in the prior art that the ability of both estrogens and antiestrogens to influence TGF$\beta$ production is dependent on the expression of estrogen receptor (ER), but the level at which this influence is exerted was not known (i.e. transcriptional, translational or post-translational). A series of experiments were therefore performed to investigate the putative dependence on ER expression of induction of reporter gene expression using the TGF$\beta$ promoter-containing constructs of the invention. Lack of ER expression virtually abolishes expression of TGF$\beta$-3, regardless of the presence of estradiol or raloxifene. It has been determined that different domains of the ER molecule are responsible for estrogen and raloxifene induction through the use of mutant ER proteins.

A. ER dependent induction of TGF$\beta$-3

Cultures of MG63 were prepared for co-transfection as in Example IV. One such culture was co-transfected with pB2-499 and pRSVER and another was co-transfected with pB2499 and pRSV vector plasmid (as a control). The ability of the following compounds to induce transcription via the raloxifene responsive element of the TGF$\beta$-3 gene was then assayed essentially as described in Example V:

(a) ethanol
(b) 17$\beta$-estradiol ($10^{-7}$M)
(c) raloxifene ($2\times10^{-6}$M)
(d) 17$\beta$-estradiol ($10^{-7}$M) and raloxifene ($2\times10^{-6}$M)

Figure 6:
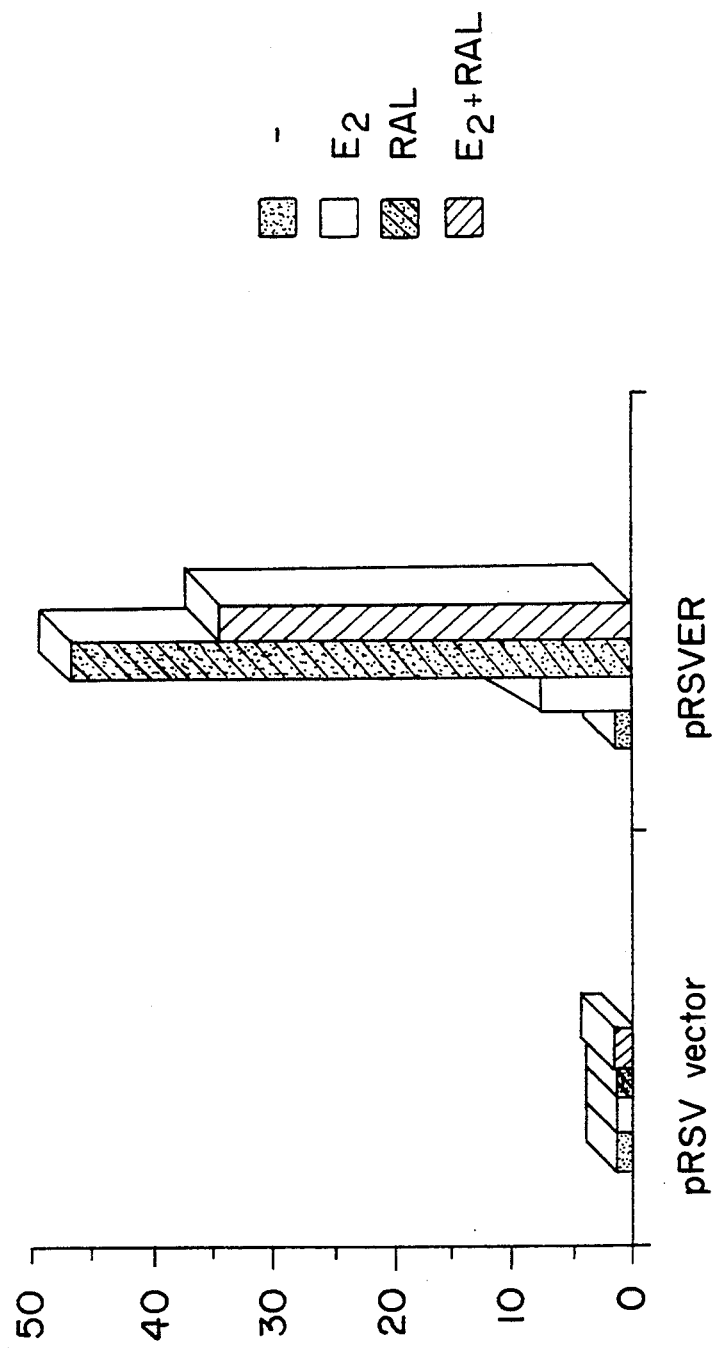
FIG. 6 is a bar graph showing the relative level of reporter gene expression in cells transfected with expression constructs containing a portion of the TGFβ-3 promoter sequence and exposed to a control compound, estrogen, raloxifene and combinations of estrogen and raloxifene in both the presence and absence of estrogen receptor. Estrogen receptor is necessary for induction of expression of the reporter gene by both estrogens and antiestrogens.

The results of one such experiment are set forth in the following Table, and a representative example of a thin-layer chromatogram produced thereby is shown in FIG. 6:

TABLE III

| | Hormone Vehicle | Estradiol | Raloxifene | Estradiol + Raloxifene |
|---|---|---|---|---|
| Control Plasmid | 0.9 | 1.0 | 1.1 | 1.2 |
| ER Expression | 1.3 | 4.6 | 45.7 | 33.7 |

TABLE III-continued

| | Hormone | | | Estradiol + |
|---|---|---|---|---|
| | Vehicle | Estradiol | Raloxifene | Raloxifene |
| Plasmid | | | | |

These results clearly indicate that ER expression is required for TGF$\beta$-3 gene promoter-mediated induction of reporter gene expression in response to estrogen, antiestrogens and combinations thereof.

B. Analysis of ER protein domains required for induction from the TGF$\beta$-3 promoter It was disclosed in the prior art that the ER protein region designated "E" is necessary for estrogen binding, while region "C" is necessary for DNA binding (see Kumar et al., 1986, EMBO J. 9: 2231–2236). It has also been well established that the "C" region is essential for ER activation of ERE-containing genes, while the "E" region is required for estrogen-dependent inducibility.

To determine the regions of the ER involved in induction of transcription from the TGF$\beta$-3 promoter, cultures of MG63 cells were prepared for co-transfection as in Example IV. Cells were transfected with mixtures of pTGF$\beta$-301LUC and one of the following expression plasmids comprising various deletion mutants of ER:

a. pCMV-ER
b. pCMV-ER$\Delta$A/B
c. pCMV-ER$\Delta$B/C/D
d. pCMV-ER$\Delta$E/F
e. pCMV-ER$_{1-530}$
f. pCMV-ER$_{L540Q}$

[see Reese & Katzenellenbogen, 1990, J. Biol. Chem. 266: 10880–10887 and FIG. 7 for a further explanation of the extent of each deletion in these plasmids].

The ability of these mutant ERs to mediate raloxifene-induced TGF$\beta$-3 activation was tested by treating cotransfected cells with vehicle (10 $\mu$L ethanol) or $10^{-7}$M raloxifene. The increase of raloxifene-induced luciferase activity over basal activity was calculated as the fold induction by raloxifene in the presence of different mutant ER forms as depicted in FIG. 7.

The results of one such experiment are shown in the following Table:

TABLE IV

| ER mutant form | vehicle | raloxifene | fold induction |
|---|---|---|---|
| pCMV-ER$_{wt}$ | 3.7 | 32.8 | 8.9 |
| pCMV-ER$\Delta$A/B | 14.2 | 39.4 | 2.8 |
| pCMV-ER$\Delta$B/C/D | 21.2 | 73.4 | 3.4 |
| pCMV-ER$\Delta$E/F | 17.4 | 20.9 | 1.2 |
| pCMV-ER$_{1-530}$ | 13.4 | 26.5 | 2.0 |
| pCMV-ER$_{L540Q}$ | 12.2 | 39.8 | 3.3 |

These results show that the hormone binding domain (i.e., the "E" region of the estrogen receptor molecule) is both necessary and sufficient to mediate raloxifene-stimulated, TGF$\beta$-3 promoter-mediated transcription of reporter genes in the reporter plasmids of the invention. The "C" region of the ER molecule appears not to be required for this process. This finding further supports the suggestion that a novel mechanism of activating gene transcription involving ER may be involved in transcription from the TGB$\beta$ promoter.

EXAMPLE VIII
Activities of Estrogen and Antiestrogens on TGF$\beta$-3 Promoter Transcriptional activation of TGF$\beta$ promoter-mediated gene expression by estrogen and antiestrogen compounds was found to be concentration-dependent. Cultures of MG63 cells were transiently co-transfected with pB-301 and pRSVER as described in Example V. Such transiently transfected cell cultures were divided into four groups of twelve cultures, and each of the four groups was used to test the ability of one estrogen or antiestrogen compound to induce transcription from the TGF$\beta$-3 promoter individually. For each group of twelve cultures, the particular estrogen or antiestrogen compound was tested in replicate cultures at six concentrations, varying in tenfold increments from $10^{-9}$M to $10^{-5}$M, as well as one set of replicate cultures treated with vehicle only (for a total of twelve cultures per experimental treatment). Hormones were dissolved in ethanol and applied to the cultures in media as described above. The four estrogens and antiestrogens tested were:

a. 17$\beta$-estradiol (Sigma Chemical Corp., St. Louis, Mo.);
b. raloxifene (Eli Lilly, Indianapolis, Ind.);
c. tamoxifen (Sigma);
d. ICI 164,384 (described in European Patent No. EP138504, issued Jul. 20, 1988).

Figure 8:
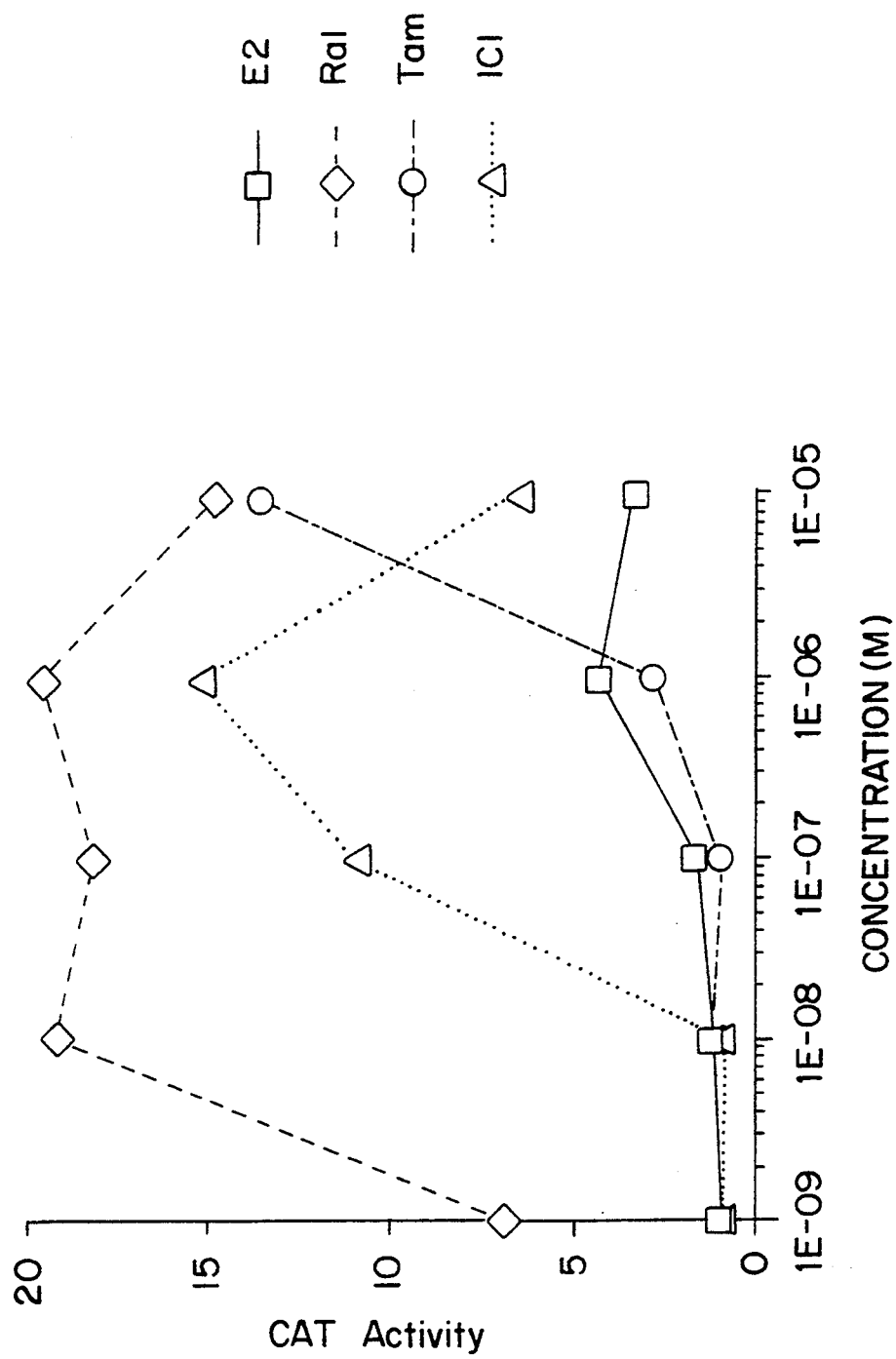
FIG. 8 depicts the levels of reporter gene expression achievable in cells transfected with an expression construct comprising the TGFβ-3 promoter and the CAT gene in the presence of various concentrations of estradiol, raloxifene, tamoxifen and ICI. In general, raloxifene is the most potent inducer at all concentrations, followed by ICI, tamoxifen. Estrogen is the least potent inducer in this system.

After 24 hours of hormone treatment (or control) the cells were washed, harvested, lysed and assayed for CAT activity as described in Example V. The results of one such experiment are tabulated below and are depicted in FIG. 8:

TABLE V

| | vehicle | $10^{-9}$M | $10^{-8}$M | $10^{-7}$M | $10^{-6}$M | $10^{-5}$M |
|---|---|---|---|---|---|---|
| estradiol | 0.85 | 0.96 | 1.1 | 1.6 | 4.3 | 3.4 |
| raloxifene | 0.85 | 6.9 | 19.2 | 18.1 | 19.6 | 14.8 |
| tamoxifen | 0.85 | 0.91 | 1.2 | 0.98 | 2.9 | 13.5 |
| ICI | 0.85 | 0.89 | 0.88 | 10.9 | 15.2 | 6.5 |

Although all estrogens and antiestrogens influence TGF$\beta$-3 promoter activity, each compound exhibits its own distinctive dose-response curve. Raloxifene is by far the more potent activator, displaying more than a 20-fold induction of reporter gene transcription and having an ED$_{50}$ at nanomolar concentrations. In contrast, estradiol showed only a 4-fold induction of reporter gene expression and an ED$_{50}$ that was two orders of magnitude higher than that of raloxifene. Tamoxifen activates the TGF$\beta$-3 promoter only at high levels (i.e., greater than micromolar). ICI showed an ED$_{50}$ of $10^{-7}$M, but this compound appears to be much less active at high concentrations ($10^{-5}$M). These results demonstrate that a novel element has been found in the promoter region of the TGF$\beta$-3 gene termed a raloxifene responsive element (RRE). This element induces transcription in the presence of both estrogens and antiestrogens and each of these compounds exhibits a characteristic dose-response profile of transcriptional activation.

EXAMPLE IX

Raloxifene-Mediated Transcriptional Activation of the TGFβ-3 Promoter in CHO and MCF-7 Cells The ability of raloxifene to induce transcription from the TGFβ-3 promoter distinct from estrogen-mediated induction was demonstrated in a variety of cell lines.

A. TGFβ-3 activation in CHO cells

Cultures of CHO cells were transiently co-transfected with pB-301 and pRSVER as described in Example IV and were used to determine the ability of both raloxifene and estradiol to induce transcription via the raloxifene responsive element. Twelve transiently transfected cultures were treated in replicate with either estradiol or raloxifene at six concentrations varying in tenfold increments from $10^{-9}$M to $10^{-5}$M (as well as a vehicle only control for a total of twelve cultures). Hormones were dissolved in ethanol and applied to the cultures in media as described above.

Figure 9:
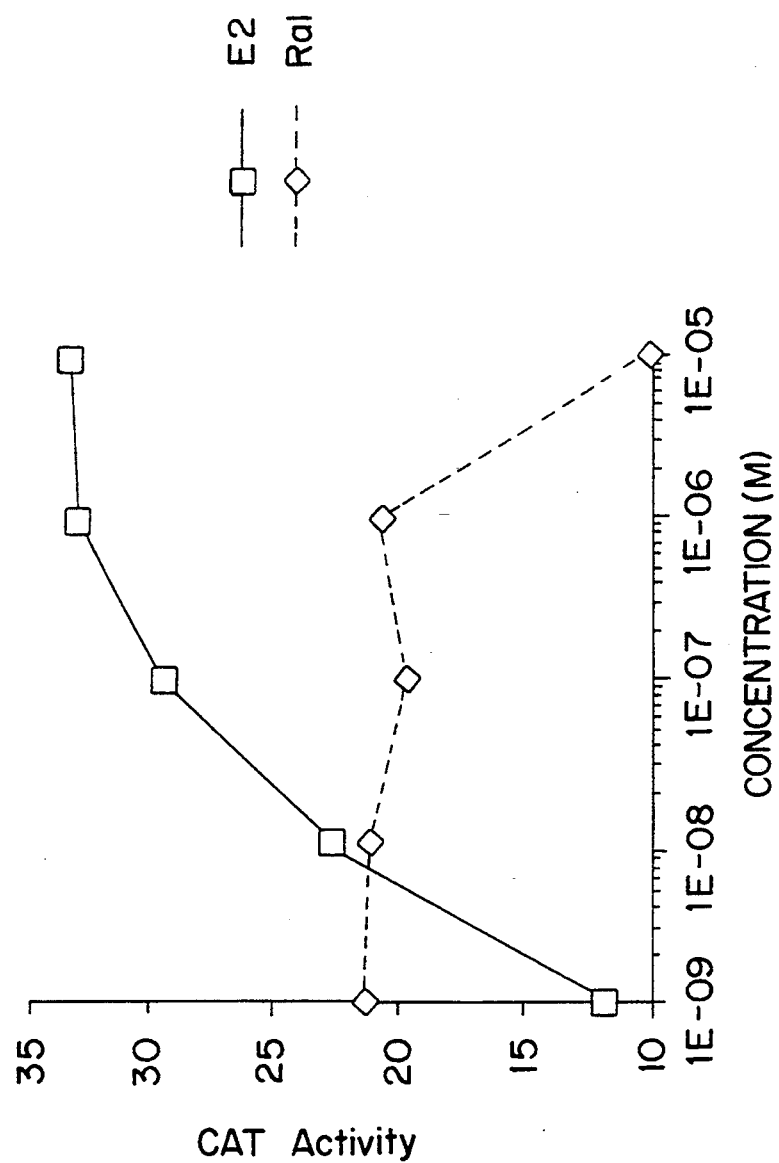
FIG. 9 depicts the relative expression of reporter gene in CHO cells transfected with an expression construct comprising a portion of the TGFβ-3 promoter and the luciferase gene in the presence of various concentrations of estradiol and raloxifene. In general, raloxifene is the more potent inducer except at low concentrations.

After 24 hours of incubation with the hormonal preparations (or the control), the cells were washed, harvested, lysed and assayed for CAT activity as described in Example V. The results are tabulated below and depicted in FIG. 9:

TABLE VI

|  | 0M | $10^{-9}$M | $10^{-8}$M | $10^{-7}$M | $10^{-6}$M | $10^{-5}$M |
|---|---|---|---|---|---|---|
| estradiol | 10.6 | 11.9 | 22.6 | 29.4 | 32.9 | 33.3 |
| raloxifene | 10.6 | 21.3 | 21.2 | 19.7 | 20.8 | 10.1 |

These results demonstrated that the previously-observed responsiveness of the TGFβ-3 promoter to estrogen and raloxifene was retained when assayed in CHO cells.

B. TGFβ-3 activation in MCF-7 cells

Cultures of MCF-7 cells were transiently transfected with pTGFβ-301LUC as described in Example IV. These cultures were used to test the ability of raloxifene and estradiol to induce transcription in this cell type. Cultures were treated with either estradiol or raloxifene at one of the following six concentrations: 0M, $10^{-9}$M, $10^{-8}$M, $10^{-7}$M, $10^{-6}$M and $10^{-5}$M. Hormones were dissolved in ethanol and applied to the cultures in media as described above.

Figure 10:
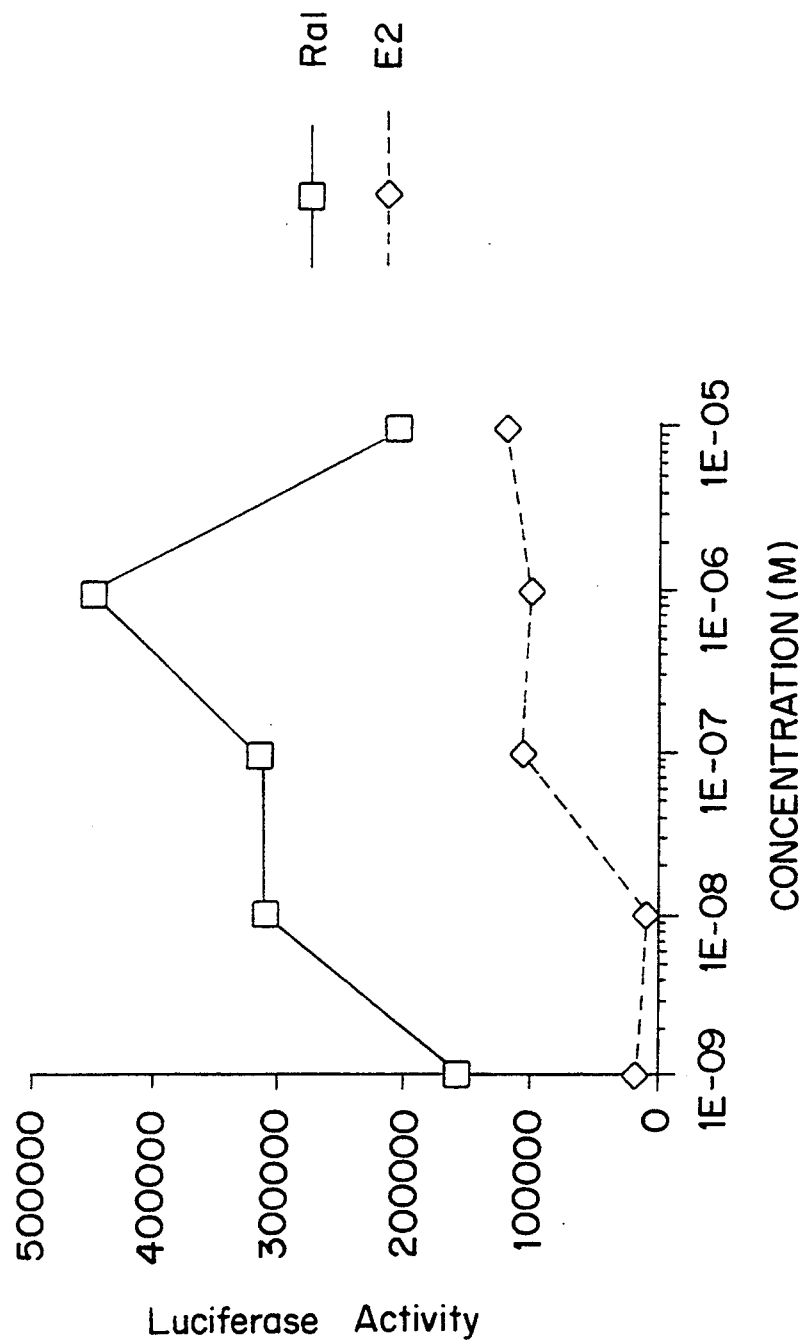
FIG. 10 depicts the relative expression of reporter gene in MCF-7 cells transfected with an expression construct comprising the TGFβ-3 promoter and the luciferase gene in the presence of various concentrations of estradiol and raloxifene. Raloxifene is the more potent inducer at all concentrations.

After 24 hours of treatment with the hormonal preparation (or the vehicle control), the cells were washed, harvested, lysed and assayed for LUC activity according to the method of Example VI. The results of this experiment are tabulated below, and the results from a series of such experiments are summarized in FIG. 10:

TABLE VII

|  | 0M | $10^{-9}$M | $10^{-8}$M | $10^{-7}$M | $10^{-6}$M | $10^{-5}$M |
|---|---|---|---|---|---|---|
| estradiol | 7.8 | 19.2 | 9.1 | 107.3 | 101.3 | 122 |
| raloxifene | 7.8 | 158 | 309 | 314 | 451 | 206 |

(Luciferase activity expressed in thousands of units)

Similar assays were performed in human endometrial cancer cells (RL59.2), human cervical cancer cells (HeLa) and monkey kidney cells (COS-1) (American Type Culture Collection, Rockville, Md.). Transcription initiated by the TGFβ-3 promoter was found to be induced by estrogen and raloxifene in all cell types tested (with variations in the magnitude of induction). These results demonstrate that estrogen- and raloxifene-mediated induction of reporter gene transcription from the TGFβ-3 promoter is not restricted to specific cell types. The different levels of induction in different cells, however, might indicate the abundance of other factors in these cells involved in regulation. The fact that raloxifene and estrogen responsiveness of the TGFβ-3 promoter were found using both luciferase and CAT as reporter genes indicates that this regulation is a general characteristic of gene expression from this promoter.

EXAMPLE X

Comparative Induction of Reporter Gene Expression from the TGFβ-3 Promoter by Raloxifene and Related Compounds Antiestrogen compounds were known in the prior art to be capable of inducing TGFβ gene expression in a dose-dependent manner (Knabbe et al., 1991, Am. J. Clin. Onc. 14 (Suppl.2): S15-S20). Furthermore, as shown in Example VIII above, raloxifene and tamoxifen were found to be capable of inducing TGFβ-3 gene expression in a dose dependent manner.

The experiments described in this Example were performed in order to correlate the ability of compounds to induce transcription via the raloxifene responsive element of the TGFβ-3 promoter with their known uterotropic capacities as demonstrated in ovariectomized rats. Seven compounds that are structurally related to raloxifene were tested for their ability to induce transcription via the raloxifene responsive element of the TGFβ-3 promoter. These Compounds can be distinguished on the basis of a spectrum of in vivo activity ranging from uterotropic (LY112676, LY81099, and LY13314) to anti-uterotropic (LY113526, LY139482 and LY177366), and included a compound known to be inert in vivo (LY98005).

The IUPAC names for the compounds and the U.S. Patents in which they have been claimed are as follows:

113526: 2-(p-hydroxyphenyl)benzo[B]thien-3-YL p-[2-(1-pyrrolidinyl)ethoxy]phenyl ketone (U.S. Pat. No. 4,133,814)

139482: [4-[2-(hexahydro-1H-azepin-1-yl)ethoxy]-phenyl][6-hydroxy-2-(4-hydroxyphenyl) benzo[B]thien-3-yl]methanone (U.S. Pat. No. 4,380,635)

177366: [6-(2,2-dimethyl-1-oxopropoxy)-2-[4-(2,2-dimethyl-1-oxopropoxy)phenyl]benzo[B]thien-3-yl][4-[2-1-piperidinyl)ethoxy]phenyl]methanone hydrochloride (U.S. Pat. No. 5,393,763, incorporated by reference)

98005: p-hydroxyphenyl3-(-hydroxyphenyl)benzo[B]-thien-2-yl ketone

112676: (p-hydroxyphenyl) 5-hydroxy-3-phenylbenzo[B]thien-2-yl ketone (U.S. Pat. No. 4,075,227)

81099: p-hydroxyphenyl 3-phenylbenzo[B]thien-2-yl ketone (U.S. Pat. No. 4,075,227)

Figure 11:
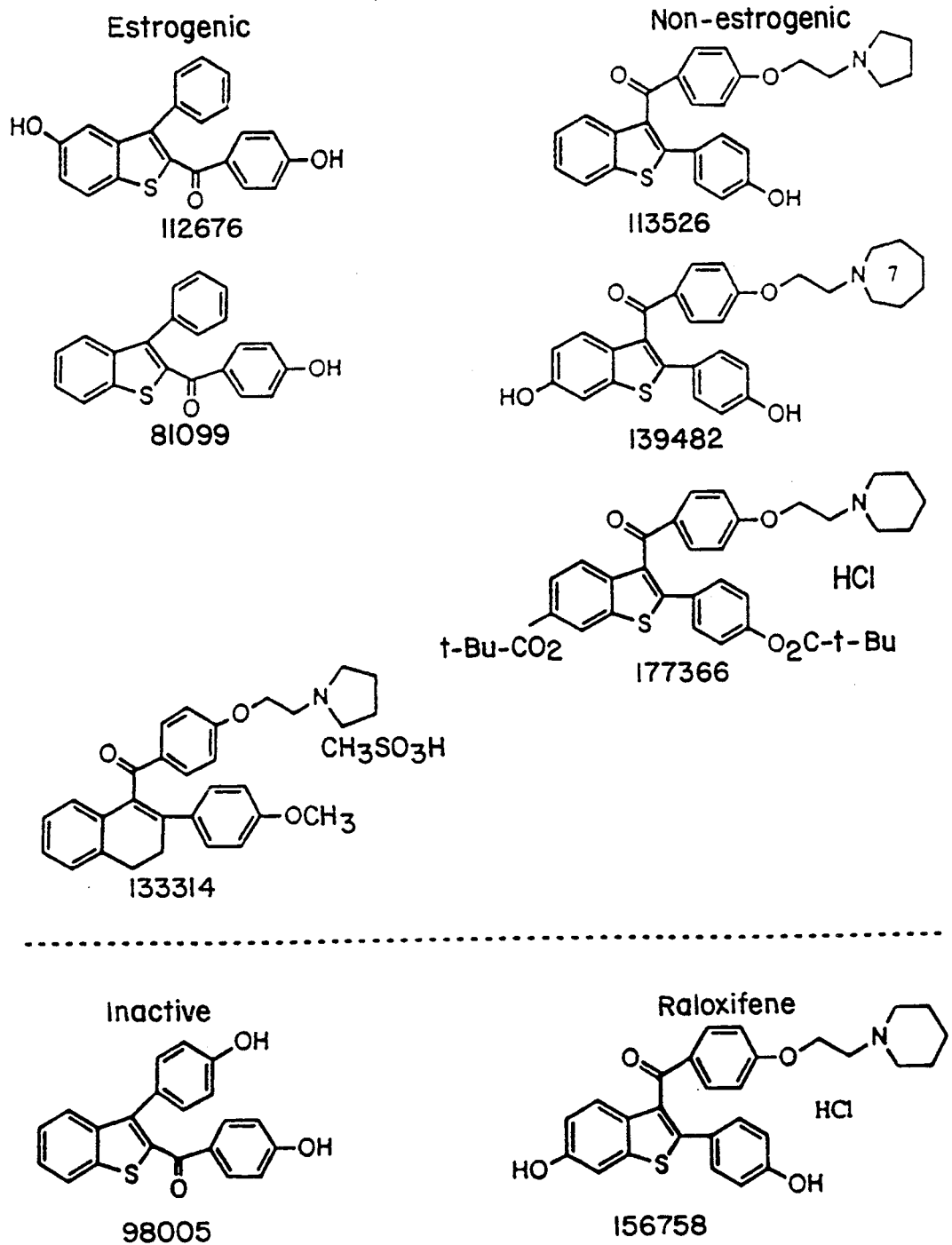
FIG. 11 represents the chemical structures of the compounds evaluated in Example X.

133314: [3,4-dihydro-2-(4-methoxyphenyl)-1-naphthanlenyl][4-[2-(1-pyrrolidinyl)ethoxy]phenyl]methanone, methanesulfonic acid salt These compounds are depicted in FIG. 11.

Figure 12:
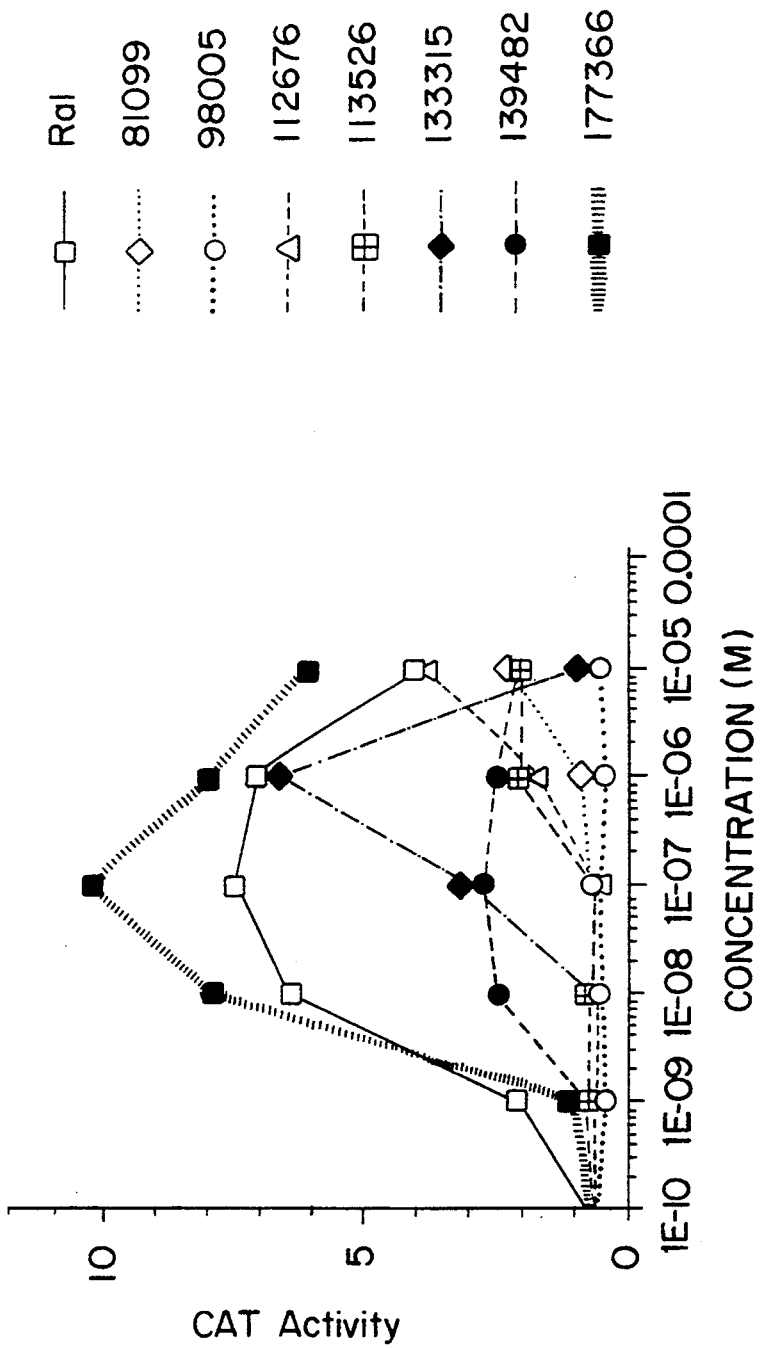
FIG. 12 represents the relative level of induction of reporter gene expression in MG63 cells transfected with TGFβ-3 promoter/CAT expression constructs and exposed to various concentrations of the compounds set forth in Example X. Overall, compound 177366 is the most potent inducer, while 98005 shows no induction.

Raloxifene, LY81099, LY98005, LY112676, LY113526, LY13314, LY139482, and LY177366 (Eli Lilly and Co.) were assayed to compare their ability to induce transcription from the promoter of the TGFβ-3 gene at varying concentrations. Cultures of MG63 cells transiently cotransfected with pB-301 and pRSVER were treated as in Example VI with the above compounds at concentrations of 0M, $10^{-9}$M, $10^{-8}$M, $10^{-7}$M, $10^{-6}$M and $10^{-5}$M. The experimental results are shown in tabular form and depicted in FIG. 12.

TABLE VIII

| | OM | $10^{-9}$M | $10^{-8}$M | $10^{-7}$M | $10^{-6}$M | $10^{-5}$M |
|---|---|---|---|---|---|---|
| raloxifene | 0.61 | 2.1 | 6.4 | 7.5 | 7.0 | 4.0 |
| LY81099 | 0.61 | 0.6 | 0.5 | 0.7 | 0.9 | 2.3 |
| LY98005 | 0.61 | 0.4 | 0.5 | 0.5 | 0.4 | 0.5 |
| LY112676 | 0.61 | 0.6 | 0.6 | 0.5 | 1.7 | 3.8 |
| LY113526 | 0.61 | 0.7 | 0.7 | 0.6 | 2.0 | 2.1 |
| LY133314 | 0.61 | 0.7 | 0.7 | 3.1 | 6.6 | 1.0 |
| LY139482 | 0.61 | 0.8 | 2.5 | 2.7 | 2.5 | 2.0 |
| LY177366 | 0.61 | 1.1 | 7.9 | 10.2 | 7.9 | 6.1 |

Compounds that displayed uterotropic properties in vivo (i.e., estrogenic compounds) showed $ED_{50}$ values of approximately $10^{-7}$M and had a relatively lower-fold induction of reporter gene expression from the TGFβ-3 promoter, much like the profile exhibited by estrogen in Example VIII. In contrast, compounds that have a profile similar to raloxifene in vivo demonstrate an $ED_{50}$ of $10^{-9}$M and a relatively greater fold induction than estrogenic compounds. (In vivo data regarding raloxifene was set forth in U.S. Pat. No. 5,393,762 and is incorporated by reference). In summary, compounds exerting estrogen like qualities in vivo show significantly less induction of transcription via the TGFβ-3 promoter than compounds that exerted antiestrogen-like qualities in vivo.

The results of these experiments demonstrate the utility of the reporter gene-containing expression plasmids described herein as a screening technique for identifying potential anti-osteoporosis agents, because those compounds that are raloxifene-like in their induction profiles and $ED_{50}$s show relatively lower uterotropic effects than estrogen-like compounds having lower induction profiles higher $ED_{50}$s in the present assay.

EXAMPLE XI

Localization of the Raloxifene Response Element in TGFβ-3 Promoter in the Region from +35 to +75

At least a portion of the raloxifene response element (RRE) in the human TGFβ-3 gene promoter was approximately localized to a particular 41 nucleotide sequence found at positions +35 through +75. This sequence was found to be necessary for mediating raloxifene-induced transcriptional activation of reporter gene expression in the TGFβ-reporter gene expression constructs described above.

Figure 13:
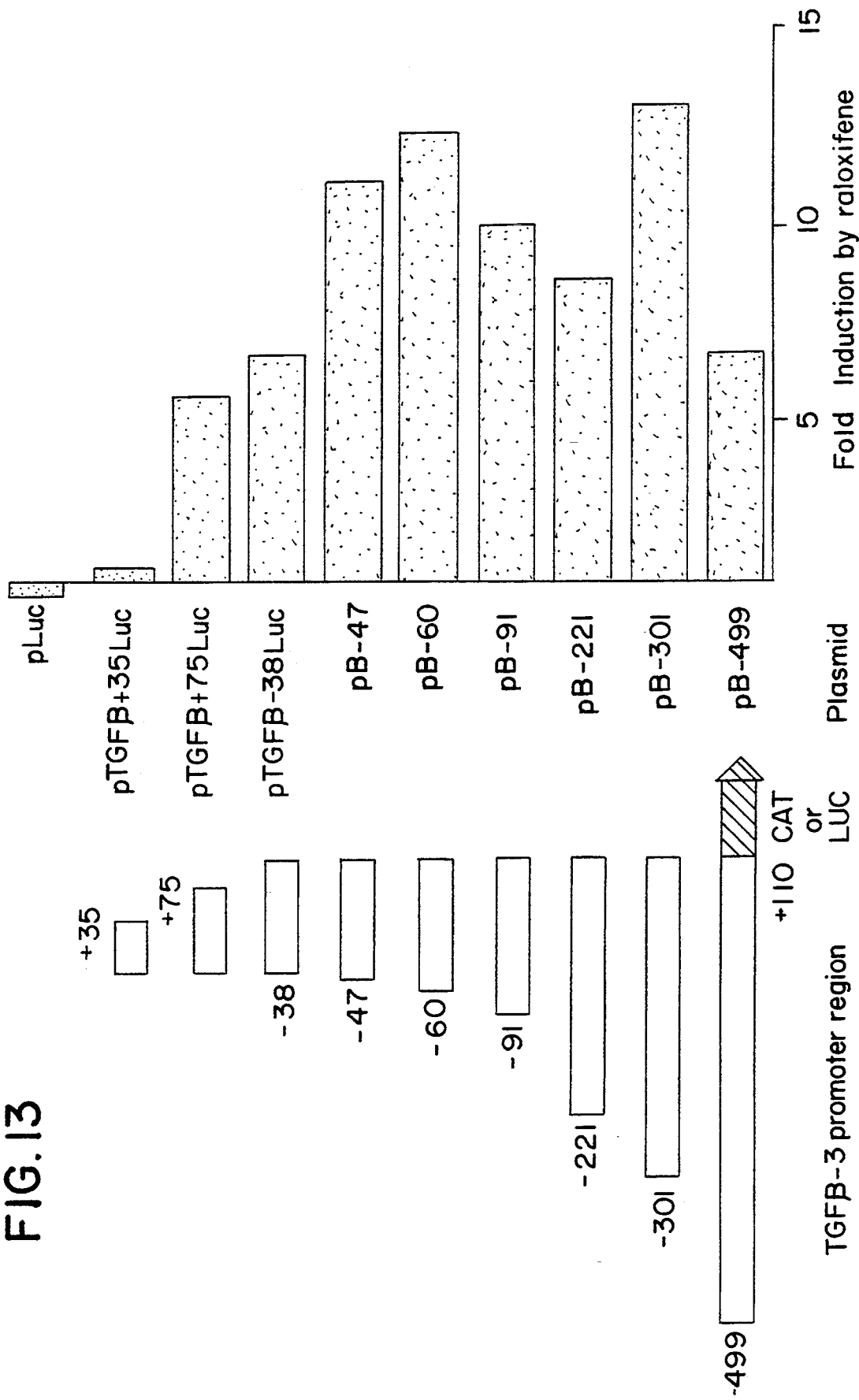
FIG. 13 depicts the portions of the TGFβ-3 promoter used to identify the 41 base pair raloxifene responsive element, and depicts the relative induction of reporter gene expression by raloxifene in cells transformed with plasmids comprising the indicated portion of the TGFβ-3 promoter sequence operably linked to a reporter gene. Although the fold induction achievable with the pB-301 construct is highest, presence of the raloxifene responsive element (base pairs +35−+75) is clearly essential for any significant induction of transcription by raloxifene in these cells.

A. Identification of a raloxifene responsive element by functional analysis of TGFβ-3 promoter deletion mutants prepared in vitro Cultures of MG63 cells transiently co-transfected with pCMVER and one of a variety of TGFβ-3 promoter deletion reporter constructs (including pB-499, pB-301, pB-221, pB-91, pB-60, pB-47, pTGFβ-38LUC, pTGFβ+75LUC, pTGFβ+35LUC and pLUC) were generated as described in Example I. These cultures were then treated with either ethanol (as a control) or $10^{-6}$M raloxifene. The degree of induction of reporter gene expression after treatment with raloxifene relative to that obtained by treatment with vehicle alone was calculated for each TGFβ-3 promoter deletion construct and are tabulated below and are depicted in FIG. 13:

TABLE IX

| Vector Plasmid | TGFβ-3 Promoter region | Fold induction by raloxifene |
|---|---|---|
| pB-499 | −499−+110 | 6.8 |
| pB-301 | −301−+110 | 13.1 |
| pB-221 | −221−+110 | 8.7 |
| pB-91 | −91−+110 | 10.1 |
| pB-60 | −60−+110 | 12.5 |
| pB-47 | −47−+110 | 11.5 |
| TGFβ − 38LUC | −38−+110 | 7.1 |
| TGFβ + 75LUC | −38−+75 | 5.8 |
| TGFβ + 35LUC | −38−+35 | 1.2 |
| pLUC vector alone | | 0.5 |

These results localize at least one portion of the raloxifene responsive element to positions +35 to +75 in the TGFβ-3 promoter sequence.

B. Nucleotide sequence of the raloxifene responsive element

Figure 14:
FIG. 14 depicts an analysis of the TGFβ-3 promoter (SEQ ID No.: 3, position 2159-2306). The major transcriptional start site and a CCCTC-motif are depicted as described in Example XI.

The nucleotide sequence of the TGFβ-3 promoter from position −38 to +110 (SEQ ID No:3, position 2159-2306) was depicted in FIG. 14. The raloxifene responsive sequence was found above to be the sequence depicted in the Figure in outline form. The open arrow indicates the major transcription start site (+1). The two black arrows indicate the two minor transcription start sites. The "TATA" sequence is shown in the open box. A putative CCCTC-motif (Lobanenekov et al., 1990, Oncogene 5:1743-1753) is indicated by a series of horizontal arrow heads under the sequence of the putative raloxifene responsive element.

Two conclusions can be drawn from the TGFβ-3 analysis. The first is that no palindromic sequences homologous to the ERE was found in this region of the TGFβ-3 promoter. This finding is consistent with the results shown in Example VII which demonstrated that DNA binding activity of ER is not required. Second, ER-mediated raloxifene activation of TGFβ-3 most likely requires other factors that are capable of binding to the raloxifene responsive sequence. A good candidate for such a protein is the CTCF factor identified by Lobanenkov et al. which is involved in c-myc gene regulation. These findings may lead to the identification of other genes as potential raloxifene inducible genes that have raloxifene responsive elements in their promoters. Furthermore, such genes could be used to identify genetic elements having the activity of raloxifene responsive elements for use in the screening procedure set forth in Example XIII.

The raloxifene responsive element of the present invention was used to search the GenBank sequence library; significant homology was found between this element and elements in the following genes:

| GenBank/EMBL Data Bank Accession No.: | Gene: |
|---|---|
| X56595 | Chicken type VI collagen α-2 |
| X55373 | Human ETS-2 promoter region |
| M30137 | Human ETS-2 (5′ flank) |
| D10231 | Mouse glucose transporter (enhancer 2) |
| M12731 | Mouse N-myc proto-oncogene |
| M13945 | Mouse pim-1 proto-oncogene |
| X63281 | R. norvegicus N-myc gene |
| X16995 | Mouse N10 gene |
| M94152 | Rat adenosine receptor |
| M20131 | Rat cytochrome P450IIE1 |
| M34111 | Rat PTHrP |
| J05097 | Rat substance P receptor |
| M64236 | Rat substance P receptor |

This finding supports the existence of this element as a discrete and important regulatory unit capable of mediating pleiotropic physiological effects in vivo in a variety of tissues and cell types.

EXAMPLE XII

Estrogen and Raloxifene Induce LDL Receptor Promoter Activation

LDL receptor expression plays an essential role in regulation of serum LDL-cholesterol uptake. It has been known that estrogen induces LDL receptor messenger RNA in vivo (Ma et al., 1986, Proc. Natl. Acad. Sci. USA 83: 792-796). As shown in this Example, this activation of LDL receptor promoter sequence by estrogen is mediated by ER. Raloxifene also induces LDL receptor promoter; however, this induction is ER independent.

A. Estrogen and antiestrogen induced LDLR-Luc production in presence of ER

Figure 15:
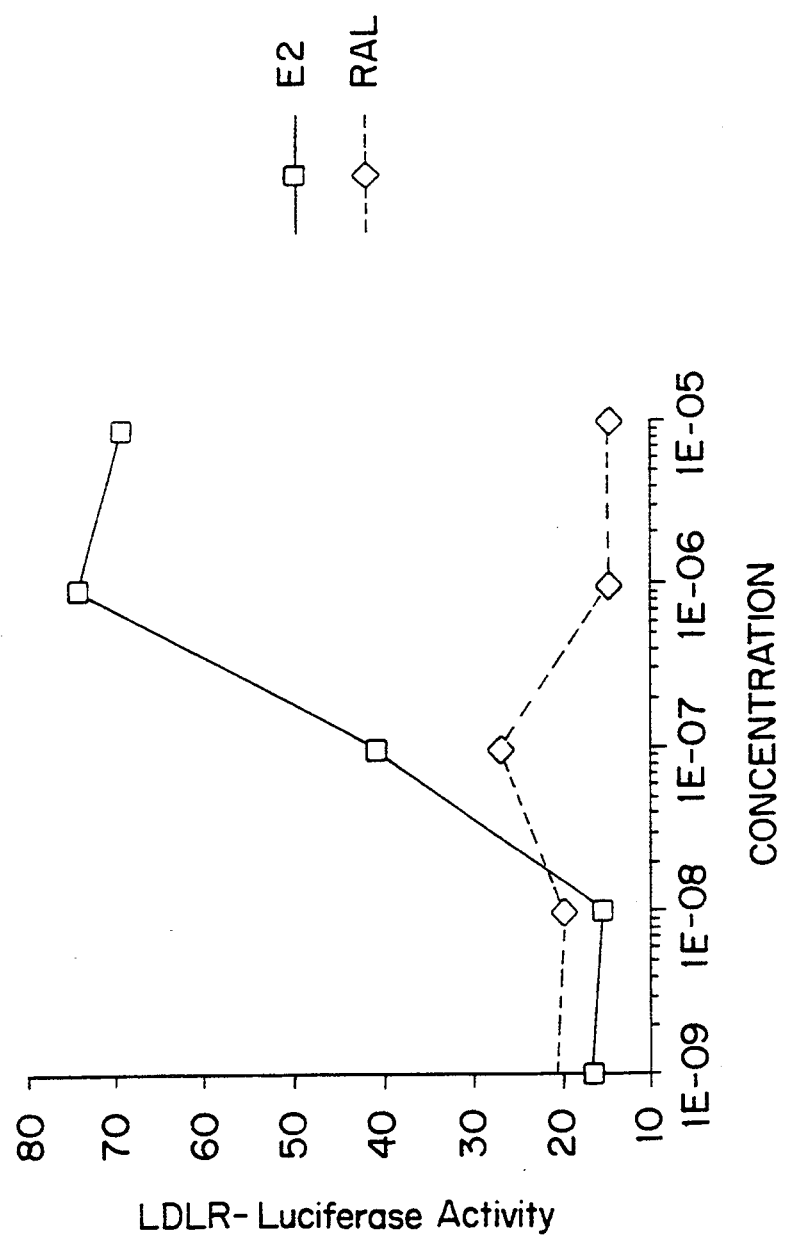
FIG. 15 depicts the relative expression of reporter gene in Hep2 cells transfected with an expression construct comprising the LDLR promoter and the luciferase gene in the presence of estrogen receptor and various concentrations of estradiol and raloxifene. Generally, raloxifene is the more potent inducer.

ATCC strain HepG2 cells were co-transfected with pLDLRLUC10 and pRSVER as described in Example IV. These cells were exposed to estradiol and raloxifene under the conditions set forth in Example VI. The results are tabulated below and a series of experiments are depicted in FIG. 15:

TABLE X

|  | 0M | $10^{-9}$M | $10^{-8}$M | $10^{-7}$M | $10^{-6}$M | $10^{-5}$M |
|---|---|---|---|---|---|---|
| estradiol | 20.9 | 16.6 | 15.4 | 40.7 | 74.0 | 69.0 |
| raloxifene | 20.9 | 20.9 | 19.9 | 26.9 | 14.6 | 14.6 |

B. Estrogen- and antiestrogen-induced LDLR-Luc production in the Absence of ER

Figure 16:
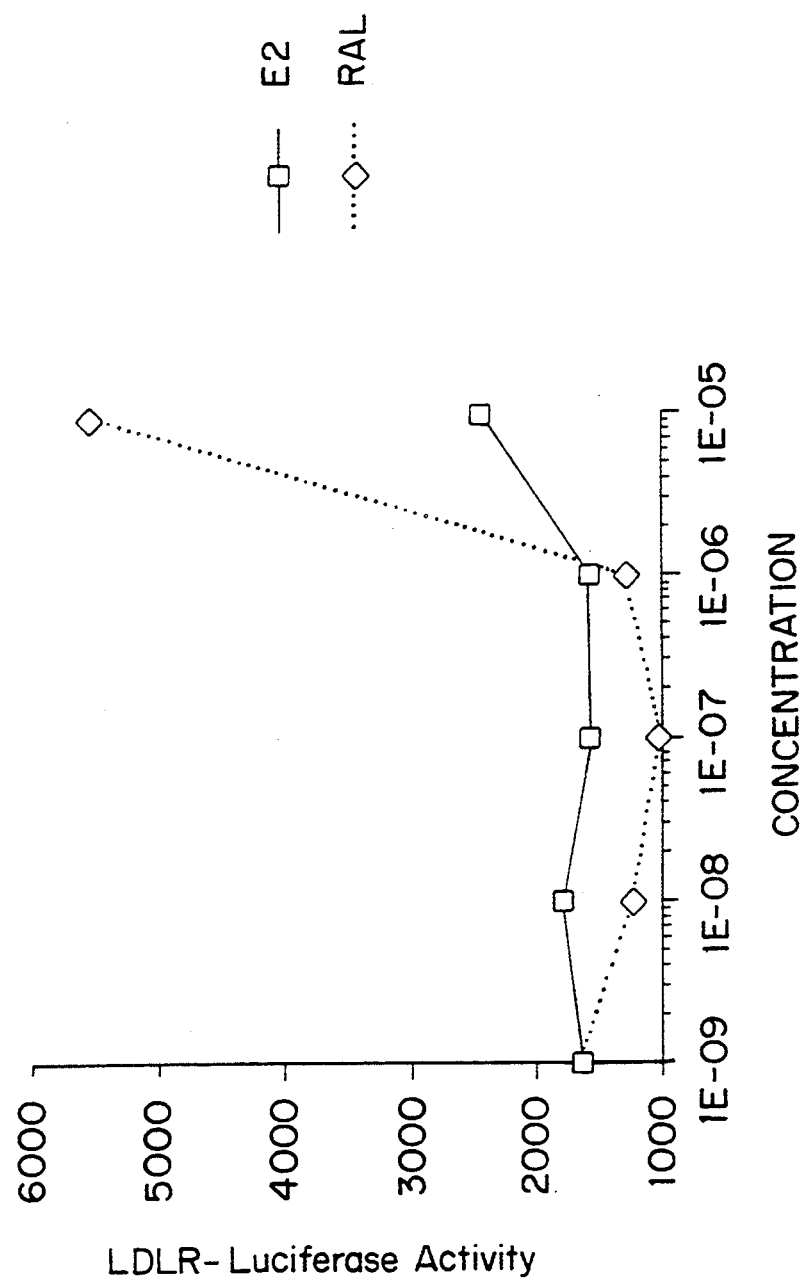
FIG. 16 depicts the relative expression of reporter gene in Hep2 cells transfected with an expression construct comprising the LDLR promoter and the luciferase gene in the presence of various concentrations of estradiol and raloxifene and in the absence of estrogen receptor. No induction is exhibited by either compound at concentrations at or below $10^{-6}$M. High concentrations of raloxifene induce expression somewhat, suggesting an alternate, non-ER dependent induction mechanism at such concentrations.

ATCC strain HepG2 cells were co-transfected with pLDLRLUC10 and pRSV vector plasmid as described in Example IV. These cells were exposed to estradiol and raloxifene under the conditions set forth in Example VI. The results are tabulated below and a representative series of such experiments are set forth in FIG. 16:

TABLE XI

|  | 0M | $10^{-9}$M | $10^{-8}$M | $10^{-7}$M | $10^{-6}$M | $10^{-5}$M |
|---|---|---|---|---|---|---|
| estradiol | 1597 | 1645 | 1792 | 1574 | 1578 | 2445 |
| raloxifene | 1597 | 1652 | 1234 | 1025 | 1291 | 5561 |

These results show that both raloxifene and estrogen have the ability to induce LDL receptor expression. This result provides an explanation of serum lipid lowering effect by estrogen and raloxifene in vivo in both animal models and humans.

EXAMPLE XIII

Method for Screening Potential Anti-Osteoporosis Agents with Potential Benefits in Lowering Lipids Based on the foregoing Examples, an assay using luciferase as a reporter gene was designed to screen for potential anti-osteoporosis agents.

Figure 17:
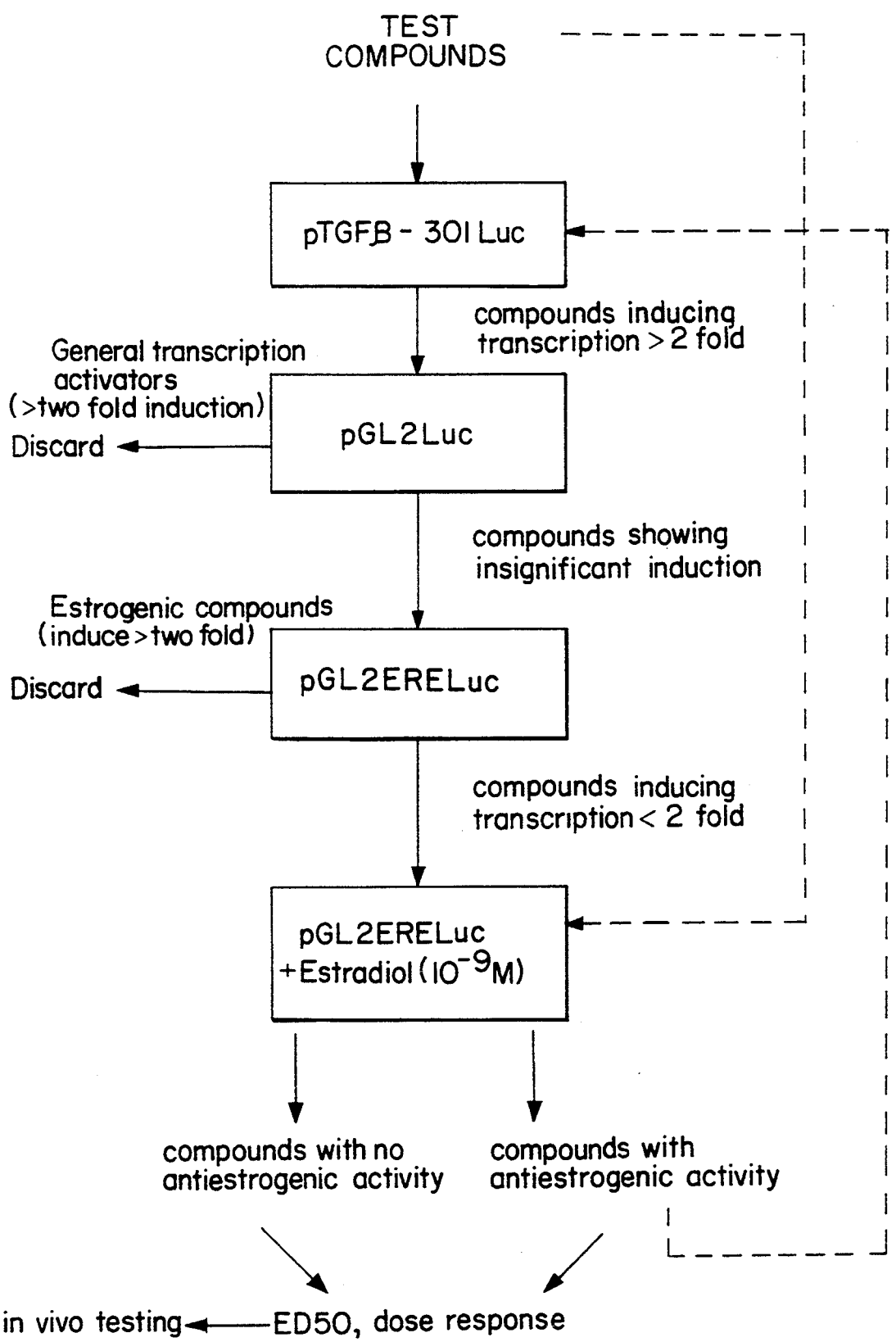
FIG. 17 is a flow diagram showing an example of a sequence of steps that can be carried out according to the teachings of the present invention to evaluate compounds with respect to their ability to induce transcription of reporter genes operably linked to the regulatory control element described herein. It is expected that a correlation will exist between compounds showing the induction profiles described in Example XIII and the ability of such compounds to act as anti-osteoporosis drugs in vivo.

Cultures of MCF-7 cells were stably transfected with:
1. pTGFβ-301LUC;
2. pGL2LUC; or
3. pGL2ERELUC;

using the methods described in Example IV. The cells are then used in the inventive method depicted in FIG. 17.

STEP 1. The first procedure that is used in the screening assay is to determine the ability of a compound to induce transcription from the TGFβ-3 promoter. The assay is performed essentially as described in Example IX, using MCF-7 cells stably transfected with pTGFβ-301LUC. Cell culture and assay conditions are adapted to the 96 well microtiter plate format. Cells are seeded in a 96-well plate at a density resulting in approximately 50% confluency. Test compounds may be selected from a variety of sources, including pharmaceutical research records, chemical manufacturers products lists, and naturally-occurring sources such as fermentation extracts. Cells are incubated in growth media (as described in Example IV) containing the test compound for about 24 hours. Cells are then lysed in situ on the plate and the lysates subjected to both a quantitative protein assay and to the luciferase activity assay. Compounds that induce a greater than two-fold increase in luciferase activity are considered competent for further testing.

STEP 2. Assays are performed with compounds identified as described in Step 1 on cell cultures that have been stably transfected with pGL2LUC to determine whether such compounds are general transcription inducers. As such general transcriptional inducers lack the transcriptional induction specificity required for potential anti-osteoporetics that are modulators of raloxifene-responsive element-dependent gene expression, such general inducers are excluded from further testing.

STEP 3. Compounds having the required transcriptional induction specificity (that is, are capable of inducing transcription induction in pTGFβ-301LUC cells without inducing transcription in cells transfected with pGL2LUC) for potential anti-osteoporetics that are modulators of raloxifene-responsive element-dependent gene expression, are then assayed to determine whether such compounds induce transcription from an estrogen responsive element. Cells stably transfected with pGL2ERELUC are assayed as described in Example VI both in the presence and in the absence of estradiol. Compounds that activate pGL2ERELUC in the absence of estrogen are disqualified for further testing, because the capacity of these compounds to induce transcription from an estrogen-responsive element in the absence of estrogen evidences potential estrogenic activity in vivo.

STEP 4. Compounds that have fulfilled the criteria of Steps 1 through 3 are then further tested to determine whether such compounds are either anti-estrogenic or non-estrogenic/non-anti-estrogenic. To this end, the compounds are assayed in the presence of estradiol in cells stably transfected with pGL2ERELUC. Inhibition of estrogen-induced luciferase activity in this assay indicates that such compounds have anti-estrogenic activity. Both anti-estrogenic and non-estrogenic compounds will be characterized for their dose-response profiles and ED$_{50}$ values. Further experiments may be done to establish the dose-response profiles of such compounds and to compare them with known anti-estrogens like raloxifene. (See Example X).

Following this screening protocol, conventional assays, particularly in vivo assay involving appropriate animal model systems may be used to further characterize the anti-estrogenic properties of the compounds identified as described herein. Development of such anti-estrogenic compounds having desirable anti-osteoporotic and/or serum lipid lowering properties may then be advantageously and expeditiously achieved from the compounds identified in this assay.

It should be understood that the foregoing disclosure emphasizes certain specific embodiments of the invention and that all modifications or alternatives equivalent thereto are within the spirit or scope of the invention as set forth in the appended claims.

---

What is claimed is:

1. A method of screening a multiplicity of compounds to identify a compound having potential as an anti-osteoporosis agent, the method comprising identifying a compound of the multiplicity that is capable of inducing transcription from a raloxifene responsive element of a mammalian promoter, that is not a non-specific transcription inducer, is not capable of inducing transcription from an estrogen-responsive element of a mammalian promoter and that is an anti-estrogenic or non-estrogenic compound, the method comprising the steps of:
   (a) assaying for the ability of the compound to induce transcription from a raloxifene responsive element of the mammalian promoter;
   (b) assaying for the inability of the compound to induce transcription from a mammalian promoter not having a raloxifene responsive element;
   (c) assaying for the inability of the compound to induce transcription from an estrogen responsive mammalian promoter; and
   (d) assaying for the ability of the compound to inhibit estrogen induction of transcription from an estrogen responsive mammalian promoter in the presence of estrogen.

2. A method of claim 1 wherein the assay of subpart (a) comprises the step of determining the ability of the compound to induce expression of a reporter gene operably linked to the mammalian promoter.

3. A method according to claim 2 wherein the assay of subpart (b) comprises the step of determining the inability of the compound to induce expression of a reporter gene operably linked to the mammalian promoter.

4. A method according to claim 2 wherein the assay of subpart (c) comprises the step of determining the inability of the compound to induce expression of a reporter gene operably linked to the mammalian promoter.

5. A method according to claim 2 wherein the assay of subpart (d) comprises the step of determining the ability of the compound to inhibit estrogen-dependent induction of expression of a reporter gene operably linked to the mammalian promoter.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 2205 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_RNA
        ( B ) LOCATION: 1..2
        ( D ) OTHER INFORMATION: /note="Number 1 corresponds to
            − 1362 of TGFB-1 promoter"

( i x ) FEATURE:
        ( A ) NAME/KEY: misc_RNA
        ( B ) LOCATION: 1363..1365
        ( D ) OTHER INFORMATION: /note="Corresponds to +1 codon of
            TGFB-1"

( x i ) SEQUENCE DESCRIPTION: SEQ ID NO:1:

```
GGATCCTTAG  CAGGGGAGTA  ACATGGATTT  GGAAAGATCA  CTTTGGCTGC  TGTGTGGGA     60
TAGATAAGAC  GGTGGGAGCC  TAGAAAGGAG  GCTGGGTTGG  AAACTCTGGG  ACAGAAACCC    120
AGAGAGGAAA  AGACTGGGCC  TGGGGTCTCC  AGTGAGTATC  AGGGAGTGGG  GAATCAGCAG    180
GAGTCTGGTC  CCCACCCATC  CCTCCTTTCC  CCTCTCTCTC  CTTTCCTGCA  GGCTGGCCCC    240
GGCTCCATTT  CCAGGTGTGG  TCCCAGGACA  GCTTTGGCCG  CTGCCAGCTT  GCAGGCTATG    300
GATTTTGCCA  TGTGCCCAGT  AGCCCGGGCA  CCCACCAGCT  GGCCTGCCCC  ACGTGGCGGC    360
CCCTGGGCAG  TTGGCGAGAA  CAGTTGGCAC  GGGCTTTCGT  GGGTGGTGGG  CCGCAGCTGC    420
TGCATGGGGA  CACCATCTAC  AGTGGGGCCG  ACCGCTATCG  CCTGCACACA  GCTGCTGGTG    480
GCACCGTGCA  CCTGGAGATC  GGCCTGCTGC  TCCGCAACTT  CGACCGCTAC  GGCGTGGAGT    540
GCTGAGGGAC  TCTGCCTCCA  ACGTCACCAC  CATCCACACC  CCGGACACCC  AGTGATGGGG    600
GAGGATGGCA  CAGTGGTCAA  GAGCACAGAC  TCTAGAGACT  GTCAGAGCTG  ACCCAGCTA     660
AGGCATGGCA  CCGCTTCTGT  CCTTTCTAGG  ACCTCGGGGT  CCCTCTGGGC  CCAGTTTCCC    720
TATCTGTAAA  TTGGGGACAG  TAAATGTATG  GGGTCGCAGG  GTGTTGAGTG  ACAGGAGGCT    780
GCTTAGCCAC  ATGGGAGGTG  CTCAGTAAAG  GAGAGCAATT  CTTACAGGTG  TCTGCCTCCT    840
GACCCTTCCA  TCCCTCAGGT  GTCCTGTTGC  CCCCTCCTCC  CACTGACACC  CTCCGGAGGC    900
CCCCATGTTG  ACAGACCCTC  CTTCTCCTAC  CTTGTTTCCC  AGCCTGACTC  TCCTTCCGTT    960
CTGGGTCCCC  CTCCTCTGGT  CGGCTCCCCT  GTGTCTCATC  CCCCGGATTA  AGCCTTCTCC   1020
GCCTGGTCCT  CTTTCTCTGG  TGACCACAC   CGCCCGCAAA  GCCACAGCGC  ATCTGGATCA   1080
CCCGCTTTGG  TGGCGCTTGG  CCGCCAGGAG  GCAGCACCCT  GTTTGCGGGG  CGGAGCCGGG   1140
GAGCCCGCCC  CCTTTCCCCC  AGGGCTGAAG  GGACCCCCT   CGGAGCCCGC  CACGCGAGA    1200
TGAGGACGGT  GGCCCAGCCC  CCCCATGCCC  TCCCCTGGG   GGCCGCCCCC  GCTCCCGCCC   1260
CGTGCGCTTC  CTGGGTGGG   CCGGGGGCGG  CTTCAAAACC  CCTGCCGAC   CAGCCGGTC    1320
CCCGCCGCCG  CCGCCCTTCG  CGCCCTGGGC  CATCTCCCTC  CCACCTCCCT  CCGCGGAGCA   1380
GCCAGACAGC  GAGGGCCCCG  GCCGGGGGCA  GGGGGGACGC  CCCGTCCGGG  GCACCCCCC    1440
```

| | | | | | | |
|---|---|---|---|---|---|---|
| GGCTCTGAGC | CGCCCGCGGG | GCCGGCCTCG | GCCCGGAGCG | GAGGAAGGAG | TCGCCGAGGA | 1500 |
| GCAGCCTGAG | GCCCCAGAGT | CTGAGACGAG | CCGCCGCCGC | CCCCGCCACT | GCGGGGAGGA | 1560 |
| GGGGGAGGAG | GAGCGGGAGG | AGGGACGAGC | TGGTCGGGAG | AAGAGGAAAA | AAACTTTTGA | 1620 |
| GACTTTTCCG | TTGCCGCTGG | GAGCCGGAGG | CGCGGGGACC | TCTTGGCGCG | ACGCTGCCCC | 1680 |
| GCGAGGAGGC | AGGACTTGGG | GACCCCAGAC | CGCCTCCCTT | TGCCGCCGGG | GACGCTTGCT | 1740 |
| CCCTCCCTGC | CCCCTACACG | GCGTCCCTCA | GGCGCCCCA | TTCCGGACCA | GCCCTCGGGA | 1800 |
| GTCGCCGACC | CGGCCTCCCG | CAAAGACTTT | TCCCCAGACC | TCGGGCGCAC | CCCCTGCACG | 1860 |
| CCGCCTTCAT | CCCCGGCCTG | TCTCCTGAGC | CCCCGCGCAT | CCTAGACCCT | TTCTCCTCCA | 1920 |
| GGAGACGGAT | CTCTCTCCGA | CCTGCCACAG | ATCCCCTATT | CAAGACCACC | CACCTTCTGG | 1980 |
| TACCAGATCG | CGCCCATCTA | GGTTATTTCC | GTGGGATACT | GAGACACCCC | CGGTCCAAGC | 2040 |
| CTCCCCTCCA | CCACTGCGCC | CTTCTCCCTG | AGGAGCCTCA | GCTTTCCCTC | GAGGCCCTCC | 2100 |
| TACCTTTTGC | CGGGAGACCC | CCAGCCCCTG | CAGGGGCGGG | GCCTCCCCAC | CACACCAGCC | 2160 |
| CTGTTCGCGC | TCTCGGCAGT | GCCGGGGGGC | GCCGCCTCCC | CCATG | | 2205 |

( 2 ) INFORMATION FOR SEQ ID NO:2:

( i ) SEQUENCE CHARACTERISTICS:
        ( A ) LENGTH: 5578 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: TATA_signal
        ( B ) LOCATION: 2248..2252

( i x ) FEATURE:
        ( A ) NAME/KEY: exon
        ( B ) LOCATION: 2278..3980

( i x ) FEATURE:
        ( A ) NAME/KEY: intron
        ( B ) LOCATION: 3981..5578

( i x ) FEATURE:
        ( A ) NAME/KEY: misc_RNA
        ( B ) LOCATION: 3635..3980
        ( D ) OTHER INFORMATION: /note="CDS, Codon start =1"

( i x ) FEATURE:
        ( A ) NAME/KEY: misc_RNA
        ( B ) LOCATION: 1..2
        ( D ) OTHER INFORMATION: /note="Number 1 corresponds to TGFB-2 —2277"

( x i ) SEQUENCE DESCRIPTION: SEQ ID NO:2:

| | | | | | | |
|---|---|---|---|---|---|---|
| AAGCTTTTAC | CAATACCTCC | CGTCTTACCC | CTCCTGGGCT | TTGGGGAAAT | TAAAGTAGCC | 60 |
| TCTTATGAGT | AAGTCAGGGG | TCTCAGGTCT | AAGGAGTTGT | TAAGTGAGCA | ATAGGTACTC | 120 |
| AGTAAACTAA | GTATTATGAA | CAAAGTGTG | TATGTCTATG | TCAGGAAGAG | GGGTGGCCAT | 180 |
| CAGAATTTAT | GGCTTGCGCT | GTTTCCTAGA | AGTGATGTAA | TGAACTTTTG | CTACTCTATC | 240 |
| CACACTCTAA | TCTGAATCTA | CTTAAGGTGC | ATCAGTGTCT | GTACCAAGAA | GGTTGTCTAT | 300 |
| AAACATGAAA | GATGGATGCT | CACTGGCTTG | TGGAAGCTGA | ACCTGTATCC | TCAGAAAATA | 360 |
| CAGTGATAGC | TAATTCAGGT | AACCAGCCAT | ATTCCACAGC | AGCATCTTCT | CTCAGTAGCT | 420 |
| CTGGTTTGGA | GCTCCTGCTC | TGTGTCTATA | ATGGCCACAG | GTGTAAGAAT | ATTCACTTTT | 480 |
| TGTCCAATCT | GTAGAGCTAG | CCTACTGCAG | TTCTCAAACT | GAACTCAGAG | GGAGGACCTA | 540 |
| ACTGGATGAA | ACTACTAGTC | TGACAGTAGC | GCCTCTTGAT | TATCTTTTTC | TTGGGCTACT | 600 |

| | | | | | |
|---|---|---|---|---|---|
| GGGATGGTAG | CTTTGCTTCA | ACTCAAAACT | GGTATCAAGG | AAAGGAACCT | GCTGGTGCTG | 660 |
| ATTTATACAT | AATTTTTAGA | ATTATTCAGA | AGTGGGTTGG | AACAATTATT | TTATTCCAGA | 720 |
| GTTTTTCAAT | GTGTGATAAT | GGAAAAATT | CTGTATTCAA | GGGAGTTTGG | AAAATGCTGG | 780 |
| GTTAAAAGAG | TGAAAAGGTT | TTCTCTTCTA | CAGGAGTTTC | AGAGCCTTTA | ACATGATAAT | 840 |
| GTTCCAGAAT | GAGGAATCTA | AGAGGACAGG | AGAGTACCCA | GTATCTCCA | AACTTGTTTG | 900 |
| ACTCCAGAAT | TCCTGTTTGT | CAGAACATAT | TCTGGGACCA | TTGTTTCTCA | GAAGTACATA | 960 |
| GTAGGTAAGA | ACATAGTGGA | TCCTGACTGC | AAAAATCCAG | CTCTACCACT | TACTGTGGTC | 1020 |
| TCGAACAAAG | TACTTAACTT | CTTTGTACCT | CAGTCTCCTC | ATCTGCCAGA | TATGGATAAT | 1080 |
| AAGACCCACT | TTATAGGTTC | ATAGTGAAGA | TTAAATGACC | ATACACAACA | CACATCAAAT | 1140 |
| TACTAAGTGT | AGTATATGTT | AGCTATTATT | ATTTTATTTA | TTCAGTGCTC | TACTAATAAC | 1200 |
| CTAGGCCCCA | TACACAACTG | AAGTATAATT | CCAAAGTGA | TAGAAAGTTC | TTTGTGACTT | 1260 |
| TTCTGAACTC | AGGAACATCT | GAAGTAGAGA | ACAGTATAGA | GATCTTGGGT | TTGGGAGTAC | 1320 |
| ATTCAACAGA | GTTTTCCAGT | TTAAATCATC | TGTCTGGTCA | GTATGGCTGC | AGAGTCATGC | 1380 |
| CGAAATGAAA | ATGTTGACTT | TGAGTAACTA | AAGGTAAAAT | AAAAGAAAAA | GGGAAGGTGG | 1440 |
| AACAGTGGTA | AGAGTTATTC | TGTATTCATC | TAATTTAAGA | CTTAGTTGAA | ATTGAAAATG | 1500 |
| TCAAGTTATG | AGTAGTGTAG | AACAAGTAGA | CATCAAACAC | TTAAAATTCC | AGCTTCCTGG | 1560 |
| ATTATGCTAT | GGAAAGAATG | AAGTTGGTGG | ATAATGTTTA | GCCTAGCAAG | AAGGTCAAGA | 1620 |
| AGAAGAAAGC | CATACAAGAA | GTGGCTTAGG | CAGCAAATTA | TAAAGGTGAC | CATTCATTCA | 1680 |
| AATCAGTAAA | ACAAACAAGT | ATACCTTATT | CTTTAGGTAA | AATTGATGGA | TCTCTGTTTT | 1740 |
| CCAGCAGTTC | ACAAACAGAG | GGGTACATTG | TAAACAACAA | ACTAACAAAA | TAAATTCTGG | 1800 |
| GATGGCAACC | TGCTAAGGTA | TCCCAGAAAA | TAAGAGGTAG | GACATGAATT | TAAAAGATTG | 1860 |
| GAAGGTATGT | CTTCAGTACT | GGCCTGGCCC | TGAGTAGACT | AGTGCCCTCC | ATAGGGGTGC | 1920 |
| GTGTGCACAC | ATAATACAGG | AGGGAAGCCT | TCCCTTCTAG | AGCAAGTGAT | TCAGCTTGGG | 1980 |
| AGGCTGTGAC | TGAGCTACAC | TAAGTAAAAA | CGGGAGACTT | GATTGTCCTT | CAACAGACCT | 2040 |
| GTCCAAAATG | ACTGGAAAGT | AAATACCGTA | AATCACTGTT | GTCAGGGCGC | ACATTCCACC | 2100 |
| TCCTTCCTCC | CTTACCCACA | GCGGTCCACA | TTTCCACACT | CCCTACACGG | TTCGGGGAGA | 2160 |
| GCTCGTGGTC | TAAGTAACGA | GAGGACTTCT | GACTGTAATC | CTAGCACGTC | ACTTTGTTGA | 2220 |
| AGGCAGACAC | GTGGTTCAGA | GAGAACTTAT | AAATCTCCCC | TCCCCGCGAA | GATCGTGATG | 2280 |
| TTATTCGCTG | GCAGCAGAAG | GTCTTGCCGA | GCGAGCTCCA | GAACGTCCTG | ACAAGAGAAA | 2340 |
| GACAGATTGA | GATAGAGATA | GAAAGAGAAA | GAGAGAAAGA | GACAGCAGAG | CGAGAGCGCA | 2400 |
| AGTGAAAGAG | GCAGGGGAGG | AGGGGGATGG | AGCATATTAC | GTGACCGGCC | TAGGGAGTCA | 2460 |
| TCCAGGAACA | AACTGAGGGG | CTGCCCGGCT | GCAGACAGGA | GGAGACAGAG | AGGATCTATT | 2520 |
| TTAGGGTGGC | AAGTGCCTCC | TACCCTAAGC | GAGCAATTCC | ACGTTGGGA | GAAGCCAGCA | 2580 |
| GAGGTTGGGA | AAGGGTGGGA | GTCCAAGGGA | CGCCCTGCG | CAACTCCCTC | AGGAATAAAA | 2640 |
| CTCCCCAGCC | AGGGTGTCGC | AAGGGCTGCC | GTTGTGATCC | GCAGGGGGTG | AACGCAACCG | 2700 |
| CGACGGCTGA | TCGTATGTGG | CTGGGTTGGC | GTTTGGAGCA | AGAGAAGGAG | GAGCAGGAGA | 2760 |
| AGGAGGGAGC | TGGAGGCTGG | AAGCGTTTGC | AAGCGGCGGC | GGCAGCAACG | TGGAGTAACC | 2820 |
| AAGCGGGTCA | GCGCGCGCGC | GCCAGGGTGT | AGGCCACGGC | GCGCAGCTCC | CAGAGCAGGA | 2880 |
| TCCGCCCGCC | CTCGGCAGCC | TCTGCGGCCC | CTGCGGCACC | CGACCGAGTA | CCGAGCGCCC | 2940 |
| TGCGAACGGC | ACCCTCCTCC | CCGCGGTGGC | TGGGCTCGCC | CCAGCGCGCA | CACGCACACA | 3000 |
| CACACACACA | CACACACACG | CACGCACACA | CGTGTCGTTC | TCTGCTCCGG | AGCTGCTGCT | 3060 |

```
GCTCCTGCTC TCAGCGCCGC AGTGGAAGGC AGGACCGAAC CGCTCCTTCT TTAAATATAT    3120
AAATTTCAGC CCAGGTCAGC CTCGGCGGCC CCCCTCACCG CGCTCCCGCC CCTCCCGTCA    3180
GTTCGCCAGC TGCCAGCCCC GGGACCTTTT CATCTCTTCC CTTTTGGCCG GAGGAGCCGA    3240
GTTCAGATCC GCCACTCCGC ACCCGAGACT GACACACTGA ACTCCACTTC CTCCTCTTAA    3300
ATTTATTTCT ACTTAATAGC CACTCGTCTC TTTTTTTCCC CATCTCATTG CTCCAAGAAT    3360
TTTTTTCTTC TTACTCGCCA AAGTCAGGGT TCCCTCTGCC CGTCCCTAT TAATATTTCC     3420
ACTTTTGGAA CTACTGGCCT TTTCTTTTTA AAGGAATTCA AGCAGGATAC GTTTTCTGT     3480
TGGGCATTGA CTAGATTGTT TGCAAAAGTT TCGCATCAAA ACAACAACA ACAAAAAACC     3540
AAACAACTCT CCTTGATCTA TACTTTGAGA ATTGTTGATT TCTTTTTTTT ATTCTGACTT    3600
TTAAAAACAA CTTTTTTTTC CACTTTTTTA AAAATGCAC TACTGTGTGC TGAGCGCTTT     3660
TCTGATCCTG CATCTGGTCA CGGTCGCGCT CAGCCTGTCT ACCTGCAGCA CACTCGATAT    3720
GGACCAGCTC ATGCGCAAGA GGATCGAGGC GATCCGCGGG CAGATCCTGA GCAAGCTGAA    3780
GCTCACCAGT CCCCCAGAAG ACTATCCTGA GCCCGAGGAA GTCCCCCGG AGGTGATTTC     3840
CATCTACAAC AGCACCAGGG ACTTGCTCCA GGAGAAGGCG AGCCGGAGGG CGGCCGCCTG    3900
CGAGCGCGAG AGGAGCGACG AAGAGTACTA CGCCAAGGAG GTTTACAAAA TAGACATGCC    3960
GCCCTTCTTC CCCTCCGAAA GTAAGTACTT ATTTGACTT CCATCCCCTG AGGTTTAGCT     4020
CTGCCCGGAG CTCTCAAAAC CGCAGCAGCT CCCGGGATCG CCCTTCCCTC TGCCGGTTCC    4080
CGTTCGCTCT TTTCCCGTTC TCCTGTCCTT CACCCCACCA CCTCCTTTTC AGTTGTAGTC    4140
TTGAGGCCAT CAGGCTTTAA AATGTTTACT TTCTACTTTA TTTTCTCCAT CTTTCCCTTG    4200
CCCCCTAACA ATGCGGTTCT TTAAAAGGCG TTATTCTCTT TTTCTTCC CTGAAGTTCT      4260
TTAGTCGGCC ACCAGCTAAG GAGTCAGCCC CACTCTGTCA AACTAGAGGT GCTCCCAGGG    4320
GCAGAGTTAA ACTGAGGAAT CTTCGTAGGT TTGTTTTCTT TGCTCCGATT GGCGTGGAGC    4380
GGCCGAACTG GTGCACGAGG GTTAAAAAAA GTGCTCTCAA AACTAGCCTC TGCCGGAAGC    4440
GCCCCCTTTC CGTGCTGACC TATCAGCTGG TTCCCCAAGC CTTCTCTATT GTCTCTAACT    4500
ACCCTAAAAA TGTCAGCATC GCCGAGACAA AACCCGGTTT GGAGACCCCT CGAGAAACCT    4560
ACCTGGCCCT CAGTCCTTGA TGTATACTTT GCTATACCTA GGTGTTTCAT TACCCACCGG    4620
CAAAATCCTA TAACCACGTT CCCTTTTCAC TTAACCTGGA GCGCAGAAAG GACAACTCCG    4680
TTTCTGACTA TGTTTTAAAA GGTTTTGTTC ACGTTATTTT TCAGCATACA CTCAAACCTG    4740
CCTTCTTCAC ATCTCCAGTG TAGCAGATCA TTTTCTTAC GGGTCTGTTA TCCTGCTCCT     4800
GCCTTTTCGT AGGCTTCCTG CAGTTACTTC AATGCATTCT TAAAACTCAG AGTAGACGAC    4860
AGCCGTATTT TTTTTTTTT TTTTACTGG CTTCTCTGAG AACAGTGTCC TCAAAACCAG      4920
CTGGCATACA GTAGCAATAG GAGTGAAATG ATTTATTGCA GAGGAAGGGA ACAGACAGTG    4980
TAGAATGATT TCAGAGTTCT TAAAAAAGA AAAAAAGAA AGAAAGAAAG AAAAGGGGCA      5040
GCAGCATCCA CTTGATACCT GAGAGGGTTA ATACCAGGA AGAAGAAAAA GAAAAGTGGG     5100
GGCGGGGTGG GGGGAACTCT TCAACATTTG TGTATTCCAA ATCCAAGTCA TAAACTTTTC    5160
ATTGGTTGCT CATTTCTCTC CTCCCCTTTC CATGCCCTAT ATACTTGCTG GCTGCCTTTG    5220
CAAAGTCTCT GTGTCTTGCC TAAATAGATA ATATAGCCTT CTTGGTAATT TTCTCTTAAA    5280
GGTTCTAGTT GCAGGGTGGT GCTTTTCTTT TTAATATTT ATTTTAGTT TGACAAGTCC      5340
TAGCTATGTG ACCTGCCATG TCTTGTACTT GATGGTCTCA GAAGTCAGCC CATGTATCTA    5400
ACCCCAGTCT TCCTAGTGAC CCTTATTTTG CTGCAGTTTC TCCTGTTCTT GTTCAATAGC    5460
AGAACAGATG CAGAGAATTC TGGCAAGCAG GATGATTTTA TTATTGTAAT TATGGCACTA    5520
```

TCCGCAACAG CTGATAAATA CACTCCACCC CTGGTTATCC CCTTTGGAAG TAAAGCTT    5578

( 2 ) INFORMATION FOR SEQ ID NO:3:

( i ) SEQUENCE CHARACTERISTICS:
        ( A ) LENGTH: 3303 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: mRNA
        ( B ) LOCATION: 2170..3303

( i x ) FEATURE:
        ( A ) NAME/KEY: mRNA
        ( B ) LOCATION: 2214..3303

( i x ) FEATURE:
        ( A ) NAME/KEY: mRNA
        ( B ) LOCATION: 2219..3303

( i x ) FEATURE:
        ( A ) NAME/KEY: misc_RNA
        ( B ) LOCATION: 3301..3303
        ( D ) OTHER INFORMATION: /note="CDS Start, codon start =1,
        translation M"

( i x ) FEATURE:
        ( A ) NAME/KEY: TATA_signal
        ( B ) LOCATION: 2170..2176

( i x ) FEATURE:
        ( A ) NAME/KEY: misc_feature
        ( B ) LOCATION: 1896..2306
        ( D ) OTHER INFORMATION: /note="pB-301 −301 to +110"

( i x ) FEATURE:
        ( A ) NAME/KEY: misc_feature
        ( B ) LOCATION: 1976..2306
        ( D ) OTHER INFORMATION: /note="pB-221 −221 to +110"

( i x ) FEATURE:
        ( A ) NAME/KEY: misc_feature
        ( B ) LOCATION: 2106..2306
        ( D ) OTHER INFORMATION: /note="pB-91 −91 to +110"

( i x ) FEATURE:
        ( A ) NAME/KEY: misc_feature
        ( B ) LOCATION: 2137..2306
        ( D ) OTHER INFORMATION: /note="pB-60 −60 to +110"

( i x ) FEATURE:
        ( A ) NAME/KEY: misc_feature
        ( B ) LOCATION: 2150..2306
        ( D ) OTHER INFORMATION: /note="pB-47 −47 to +110"

( i x ) FEATURE:
        ( A ) NAME/KEY: misc_feature
        ( B ) LOCATION: 2159..2306
        ( D ) OTHER INFORMATION: /note="pB-38 −38 to +110"

( i x ) FEATURE:
        ( A ) NAME/KEY: misc_feature
        ( B ) LOCATION: 2159..2271
        ( D ) OTHER INFORMATION: /note="TGFB-3 position −38 to
        + 75"

( i x ) FEATURE:
        ( A ) NAME/KEY: misc_feature
        ( B ) LOCATION: 2159..2231
        ( D ) OTHER INFORMATION: /note="TGFB-3 position −38 to
        + 35"

( x i ) SEQUENCE DESCRIPTION: SEQ ID NO:3:

CAGTAGTAGC TTCCAGAACT TGCTTAGCAC CTGAATCACG TGTGAGGTTT GTAAAGAAAC    60

-continued

| | | | | |
|---|---|---|---|---|
|AGAGATGCCA|GGGCCTCAGC|TCTGGAGACT|GATTGGTAGA|GGTGGAGTCC AAAAAAGTAT| 120
|AACTTTAATA|ATTTTCCTTC|CTATCTTCAA|CTGTCTGCTC|AAAGGCCTTC CCTTATCACC| 180
|CTATTTGAAA|CTGCAACATC|CCCCAACCTA|GGCACACCCC|ATCCTCCTTC CCTGCTTGAT| 240
|TTTCTGCCAC|ACCACATTTG|TTTGTTTGCT|TGTCTGTTTG|AGACACGGTC TTGCTCTGTC| 300
|GTCCAGGCTG|GAGTGCAGTG|GTGCAATCTT|GGCCCCTGT|AAACTCGCCT CCCTGGCTCA| 360
|AGTGATTATC|CTGCTCAGCC|TCCCAAGTAG|ATGCGTGCGC|CAACATGCCG GGCTAATTTT| 420
|TCCATTTTTT|TGTAGAGACT|GGGTTTCGCC|GTGTTGCTGG|GGCTGGTCTC GAATTCCTGA| 480
|GCTCAAGTAA|TCCTCCTGCA|TGGGCCTCCC|CAAATGCTGG|GATTACAGGC GTGAGCCACT| 540
|GCACCTGGCT|CAGCACTTTT|TACCGTACTA|CATCATTTAC|ATATTTATTT AGTTTATCGC| 600
|CTCCTCCACT|GCCCCACCCC|TGCCTCTAAA|TAAATTTCC|CTGAGGGCAG GAGTTTTGTT| 660
|TCGTTCACTG|ATATTCTTCA|CAGAGCCTAG|AATAGTGCCT|GGTATATAGA AACATTAAAC| 720
|TTTTTCTGAA|ATTTCAGAGG|CAGTATAGCA|TAGTAATTAA|GTCCAGAATC TGGCAACGTC| 780
|CTGGGTGCAA|ATCCCAACAG|CTGACACCTA|ATAACTATGT|GACCTTGGGC AAGTTACTTT| 840
|TAAAGTTTCT|ACCCCTAGGT|TTCCCATTGG|TTTTGCAAAT|GAAAGTAATG CCTACCCAAG| 900
|CTAGATAGCC|TGTGTAAATA|TCGCCTCCAT|CACTCACAAG|CAGTGTGGTC TGTAAAAAAA| 960
|AAAACAAAAA|ACTCTATGCC|TCAGTTTCCT|CATCCGTAAA|AGTGACCCAC CGCTGTGCTG| 1020
|GGATACAGAG|AACAGCCCCT|TCAGTTAGTG|GCCTGGAAGC|CAGCCTCTCA GAAAGGGTCC| 1080
|AGGAAGGCTG|GAGTGAGATG|GGGTGGAGCG|GCACTCACTC|TCAGGAAAGT TCAGTTCAGA| 1140
|GGCAAGCCCT|GTGTTGCGGG|GTGCGGGGAG|CCACGTGCCC|TACCCTCCCT TGGCTGCTCG| 1200
|TGGGAAAAGG|CCTAGAGGTT|CGGGCCGAGA|AGAGGAGCGA|AGCACAGAG CCGACTTCCC| 1260
|CTCACCCATC|TGGGAAATGG|CTCGGGCCAA|CTGCTGACTT|CGCGCTCGCT GGCCGACGTC| 1320
|CTGCGGAGAC|CTCGGCGGGG|AGGGAGGCTG|AACATCTGGA|TGACATTTCT GCGAGAGAGC| 1380
|GGCTCCGGAG|CGGCGGTCGG|GGAGGGAGAG|CTGCTCGTGC|GCACGTCGGG CCGGGAGGGA| 1440
|GGCGATTCCT|CGGGGCCTGG|GTCTTGTTTT|TCTCGCTCTC|TACCGCAGCC CCTTCTCCCG| 1500
|CCCCTCAGCC|CCCACCCCGC|AGCCCCAGC|CCCCGAGCCT|CCCCGGCTCC CGACCAGCCG| 1560
|AGCTCCTTCA|CTGGCGGCCT|CCGCTCGCCA|GAGGGCACCC|TCGATCTTCC GGAAAACGCC| 1620
|ACCATTTTTC|ACTGCCCCTG|GAGCGTCTCC|AGGCTTCTGC|CCGCCTCCCG ACTCCGATCT| 1680
|TGTCAATGAA|GAATCGGGCC|AGGATCGCCG|CGGAGCGGAC|GCCGACCCTC CGACCCGGCT| 1740
|CGCAGGCTGG|GAGTCCCCTC|TGCGAGGCTG|GCATGGCCGC|CCCTACCGGG TCCCGCGCCC| 1800
|TCTGCGGACC|CTCCCCGGGT|TGGGCCTGGC|CGCGGGCGGC|CCCGGGACCG GGGACCAGG| 1860
|AGGGAGAGTA|GACCGGGCCG|GACGGCGCGG|ACTGACAGCT|GGCGAGAGGG CGCCGGGGCT| 1920
|GGGGGAAAGG|GAGGGAGGGG|GCTCATCGGA|GTAACTTTCC|AGAAAAACAC CAACGTGTGG| 1980
|CAGGAGTGAT|TCCAAGAGGG|GAAAAAAAGT|TCAGCTACCA|CGTCGAACGA GAGGACTCGC| 2040
|AAAGTATTTT|TCAAAAGGGC|TCGGCTTTTC|CTGTGCCTGT|TTAAAACATT AACATCGTGC| 2100
|AGCAAAAGAG|GCTGCGTGCG|CTGGTCCCTC|CCTCCCCCAC|CCCAGGCCAG AGACGTCATG| 2160
|GGAGGGAGGT|ATAAAATTTC|AGCAGAGAGA|AATAGAGAAA|GCAGTGTGTG TGCATGTGTG| 2220
|TGTGTGTGAG|AGAGAGAGGG|AGAGGAGCGA|GAGGGAGAGG|GAGAGGGAGA GAGAGAAAGG| 2280
|GAGGGAAGCA|GAGAGTCAAG|TCCAAGGGAA|TGACCGAGAG|AGGCAGAGAC AGGGGAAGAG| 2340
|GCGTGCGAGA|GAAGGAATAA|CAGCAGCTTT|CCGGAGCAGG|CGTGCCGTGA ACTGGCTTCT| 2400
|ATTTTATTTT|ATTTTTTTCT|CCTTTTTATT|TTTAAAGAG|AAGCAGGGGA CAGAAGCAAT| 2460
|GGCCGAGGCA|GAAGACAAGC|CGAGGTGCTG|GTGACCCTGG|GCGTCTGAGT GGATGATTGG| 2520

( i i ) MOLECULE TYPE: cDNA ( x i ) SEQUENCE DESCRIPTION: SEQ ID NO:7:

GATCTCTCCA GTCGCGA                                              17

( 2 ) INFORMATION FOR SEQ ID NO:8:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

TCGAGAAAAG TCAGGTCACA GTGACCTGAT CAAAC                           35

( 2 ) INFORMATION FOR SEQ ID NO:9:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

TCGAGTTTGA TCAGGTCACT GTGACCTGAC TTTTC                           35